(12) United States Patent
Callewaert et al.

(10) Patent No.: US 11,181,527 B2
(45) Date of Patent: Nov. 23, 2021

(54) MEANS AND METHODS FOR MONITORING INFLAMMATION

(71) Applicants: VIB VZW, Ghent (BE); Universiteit Gent, Ghent (BE)

(72) Inventors: Nico L. M. Callewaert, Nevele (BE); Dieter Vanderschaeghe, Lokeren (BE); Tom Raes, Ghent (BE)

(73) Assignees: VIB VZW, Ghent (BE); Universiteit Gent, Ghent (BE)

( * ) Notice: Subject to any disclaimer, the term of this patent is extended or adjusted under 35 U.S.C. 154(b) by 242 days.

(21) Appl. No.: 15/753,880

(22) PCT Filed: Aug. 26, 2016

(86) PCT No.: PCT/EP2016/070223
§ 371 (c)(1),
(2) Date: Feb. 20, 2018

(87) PCT Pub. No.: WO2017/032888
PCT Pub. Date: Mar. 2, 2017

(65) Prior Publication Data
US 2018/0238898 A1    Aug. 23, 2018

(30) Foreign Application Priority Data
Aug. 26, 2015   (EP) .................................... 15182464

(51) Int. Cl.
*G01N 33/66*        (2006.01)

(52) U.S. Cl.
CPC .................................... *G01N 33/66* (2013.01)

(58) Field of Classification Search
CPC .... C07K 2317/41; C07K 16/40; A61K 47/68; A61K 47/6871; G01N 33/66
See application file for complete search history.

(56) References Cited

U.S. PATENT DOCUMENTS

2008/0318332 A1   12/2008  Mechref et al.

FOREIGN PATENT DOCUMENTS

| WO | 03087833 A2 | 10/2003 | |
|---|---|---|---|
| WO | 2004063753 A2 | 7/2004 | |
| WO | 2006114663 A1 | 11/2006 | |
| WO | WO-2014065661 A * | 5/2014 | ............ A61K 47/48 |
| WO | 2017032888 A1 | 3/2017 | |

OTHER PUBLICATIONS

Blomme et al. N-glycan based biomarker distinguishing non-alcoholic steatohepatitis from steatosis independently of fibrosis. Digestive and Liver Disease. 2012;44:315-322.*
Allhorn et al. Human IgG/FcγR Interactions Are Modulated by Streptococcal IgG Glycan Hydrolysis. PLoS ONE. 2008;3(1):e1413.*
Collin et al., EndoS, a novel secreted protein from *Streptococcus pyogenes* with endoglycosidase activity on human IgG, Embo Journal, Jun. 15, 2001, pp. 3046-3055, vol. 20, No. 12, Oxford University Press, Surrey, GB.
Bloome et al., N-glycan based biomarker distinguishing non-alcoholic steatohepatitis from steatosis independently of fibrosis, Digestive and Liver Disease, 2012, pp. 315-322, vol. 44, No. 4.
PCT International Search Report, PCT/EP2016/070223, dated Nov. 22, 2016.
PCT International Written Opinion, PCT/EP2015/076995, dated Nov. 22, 2016.
SIGMA-ALDRICH, Product Information: IgGZERO from Streptococcus Pyogenes Recombinant, Expressed in *E. coli*. (2014) www.sigma-aldrich.com, accessed Jul. 9, 2020, 2 pages.

* cited by examiner

*Primary Examiner* — Lynn Y Fan
(74) *Attorney, Agent, or Firm* — Patent Law Works, LLP

(57) ABSTRACT

The application discloses methods, kits and a novel biomarker to detect and/or to prognose inflammation in patients. The diagnostic test is based on measuring the ratio of galactosylated and non-galactosylated specific N-glycans as obtained by enzymatic treatment of the total mixture of proteins present in a body fluid such as blood, serum or plasma.

8 Claims, 18 Drawing Sheets
(15 of 18 Drawing Sheet(s) Filed in Color)

MEANS AND METHODS FOR MONITORING INFLAMMATION

CROSS-REFERENCE TO RELATED APPLICATIONS

This application is a national phase entry under 35 U.S.C. § 371 of International Patent Application PCT/EP2016/070223, filed Aug. 26, 2016, designating the United States of America and published in English as International Patent Publication WO 2017/032888 A1 on Mar. 2, 2017, which claims the benefit under Article 8 of the Patent Cooperation Treaty to European Patent Application Serial No. 15182464.6, filed Aug. 26, 2015.

TECHNICAL FIELD

This application discloses methods, kits and a novel biomarker to detect and/or to prognose inflammation in patients. The diagnostic test is based on measuring the ratio of galactosylated and non-galactosylated specific N-glycans as obtained by enzymatic treatment of the total mixture of proteins present in a body fluid such as blood, serum or plasma.

BACKGROUND

Immunoglobulin G (IgG) glycosylation has been studied for more than 30 years. The level of IgG core-fucosylation is inversely proportional with antibody-dependent cellular cytotoxicity, whereas sialylation might play an anti-inflammatory role. A large amount of studies focused on IgG galactosylation in a broad range of chronic inflammatory diseases such as rheumatoid arthritis,[1] ankylosing spondylitis, advanced cancer,[2] tuberculosis,[3] inflammatory bowel disease,[4] chronic liver disease,[5] etc. In these conditions, the N-glycans of the Fc domain (representing over 80% of the total IgG N-glycan pool) are showing a reduced efficiency in beta-1,4-galactosylation compared to healthy controls. Interestingly, treatment of these patients normalizes the galactosylation level as shown for, e.g., RA patients[6] and chronic hepatitis B patients.[7] In the latter, it was shown that the severity of necroinflammation correlated with the level of IgG undergalactosylation.

Chronic inflammation is a hallmark of many diseases that affect more than 5% of the population. Rheumatoid arthritis, chronic liver disease, and inflammatory bowel disease are chronic necroinflammatory diseases of which the incidence is rapidly rising. Prolonged exposure to inflammation in these diseases could result in permanent tissue damage, causing disability. Therefore, measuring chronic exposure to inflammation would allow assessing the severity of the disease, monitoring therapy efficacy in these patients, and adjusting therapy accordingly. Many treatment regimens for chronic inflammatory disease are extremely expensive (e.g., anti-TNF biologicals) and come with significant side effects and, for this reason, objective efficacy monitoring is highly desirable. However, the mainstay inflammation marker (C-reactive protein) fluctuates on a daily basis and is, therefore, inherently unsuitable to monitor chronic disease activity. In contrast, the inflammatory processes that lead to IgG galactosylation changes need to persist for at least 1-2 half-lives (i.e., 24 days) of the IgG pool to become noticeable.

Yet another test that is performed in the clinic is the sedimentation rate of red blood cells (ESR). This is increased during inflammation due to an unknown mechanism of zeta-potential changes of red blood cells that allow for cell clumping. This is a 100-year-old inexpensive test that is routinely conducted at high frequency. It is not used for specific diagnosis, but as an aid to determine how active a disease with an inflammatory component is. ESR is increased in several conditions including infection, acute/chronic inflammation and cancer. It does not fluctuate as rapidly as CRP, but the latter is considered as a better marker for inflammation as it is not affected by as many other interfering processes. IgG galactosylation as a biomarker has been widely studied for monitoring the progression of patients with different diseases, hallmarked with a chronic inflammatory component. Its potential in measuring the exposure to inflammation over a period of several weeks is, however, highly unexplored. The marker is also currently not used in the clinic because of the technical clinical chemistry complexity of pulling out IgG from the body fluid such as serum or plasma for subsequent biochemical analysis of the glycosylation thereof. There is a need to develop a robust method to release a subset of analyzable N-glycans or fragments derived thereof from the total mixture of proteins in body fluids such as serum or plasma, in such way that the IgG galactosylation status can be derived therefrom without the need for laborious and difficult standardized IgG purification from blood. This disclosure satisfies this need.

The total mixture of proteins in body fluids like serum, plasma or blood, is highly complex and incompletely characterized in its composition. Many enzymes are known to be able to release N-glycans or fragments thereof from proteins. Some of these enzymes, such as the endoglycosidase S (Endo S), have been described, release N-glycan fragments from IgG. However, because of the high and only partially characterized complexity of the body fluid glycoprotein composition, it is unpredictable under which conditions, if any, any such enzyme could release a glycan (fragment) mixture that would not be contaminated with glycans derived from off-target (i.e., non-IgG) proteins in the mixture, thus obfuscating conclusions on the IgG glycosylation status.

BRIEF SUMMARY

As a basis for this disclosure, it was discovered that adding the endoglycosidase endoS to the total mixture of proteins in a body fluid-like serum releases a panel of N-glycan fragments that can be analyzed for their relative abundance and yields biomarkers that correlate very tightly with biomarkers derived from PNGaseF-released N-glycans from purified IgG from such sera use. Surprisingly, it was found that Endo S is only truly IgG-specific when used in buffer conditions having a pH higher than 7.4, which is higher than the physiological pH in blood. Indeed, when no care is taken about reaction conditions, other antibody types such as IgA and IgM are also partially deglycosylated. Furthermore, it was found that IgG-linked N-glycans modified with bisecting GlcNAc are not released by Endo S, and also that desialylating the serum protein IgA and IgM glycans prior to Endo S treatment results in non-IgG glycans also being released from the serum protein mixture. Consequently, to use endo S for selective IgG glycan fragment release from the total mixture of proteins present in serum such that the released glycan fragment mixture is useful for measuring specific IgG glycosylation changes, requires precautions unknown in the art. In addition, the optimal glycan profile was identified after digestion with Endo S of the glycoconjugates present in a body fluid. The hereby obtained biomarker is a reliable marker for measuring (diagnosing or prognosing) the galactosylation of glycans present in body samples from patients suffering from inflammation.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7A) UGS1 on PNGase F purified IgG and UGS4 on PNGase F purified IgG. FIG. 7B) UGS1 on PNGase F purified IgG and UGS4 on Endo S serum. FIG. 7C) UGS4 on PNGase F purified IgG and UGS 4 on Endo S serum. FIG. 7D) UGS4 on Endo S purified IgG and UGS4 on Endo S serum.

DETAILED DESCRIPTION

Figure 1A:
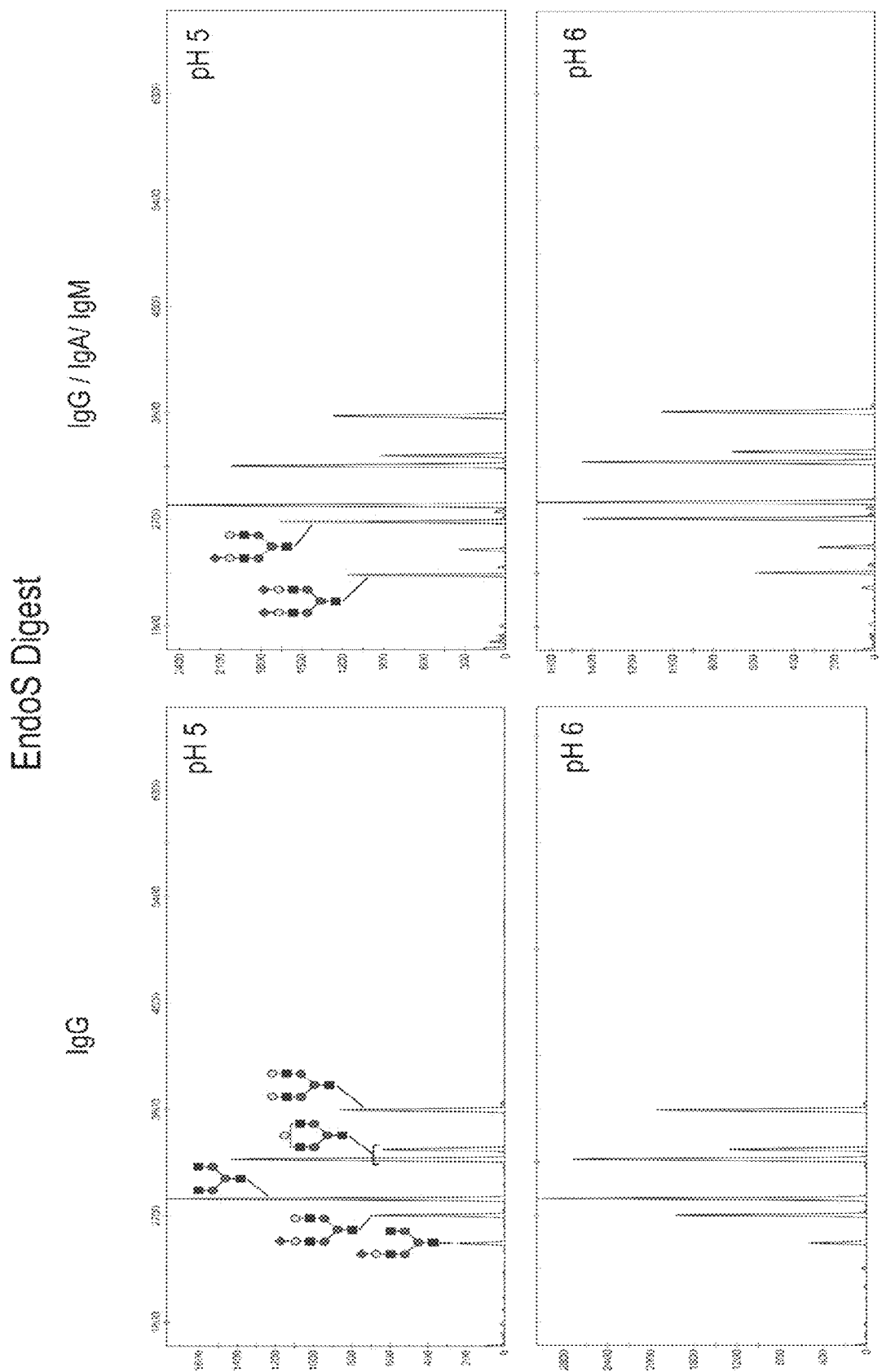
FIGS. 1A and 1B: Endo S digest on IgG (left panel) versus a mixture of IgG, IgA and IgM. Reaction conditions were kept constant except for the pH at which the digestion was carried out. Peaks indicated in black represent N-glycans that are cleaved from IgG. Each (fraction of) peak marked in red represents glycans derived from IgA and IgM.

This disclosure is described with respect to particular embodiments and with reference to certain drawings but is not limited thereto but only by the claims. Any reference signs in the claims shall not be construed as limiting the scope. The drawings described are only schematic and are non-limiting. In the drawings, the size of some of the elements may be exaggerated and not drawn to scale for illustrative purposes. Where the term "comprising" is used in the present description and claims, it does not exclude other elements or steps. Where an indefinite or definite article is used when referring to a singular noun, e.g., "a," "an," or "the," this includes a plural of that noun unless something else is specifically stated. Furthermore, the terms "first," "second," "third," and the like, in the description and in the claims, are used for distinguishing between similar elements and not necessarily for describing a sequential or chronological order. It is to be understood that the terms so used are interchangeable under appropriate circumstances and that the embodiments of the disclosure described herein are capable of operation in other sequences than described or illustrated herein.

The following terms or definitions are provided solely to aid in the understanding of the disclosure. Unless specifically defined herein, all terms used herein have the same meaning as they would to one skilled in the art of this disclosure. Practitioners are particularly directed to Sambrook et al., *Molecular Cloning: A Laboratory Manual*, 4$^{th}$ ed., Cold Spring Harbor Press, Plainsview, N.Y. (2012); and Ausubel et al., *Current Protocols in Molecular Biology* (Supplement 100), John Wiley & Sons, New York (2012), for definitions and terms of the art. The definitions provided herein should not be construed to have a scope less than understood by a person of ordinary skill in the art.

The endoglycosidase S (abbreviated herein also as "Endo S") is an enzyme that was first described by Mattias Colin and Arne Olsén in 2001.[8] Endo S is described in the art as specifically acting on the chitobiose (i.e., GlcNAc-GlcNAc) core of the asparagine-linked glycan of human IgG. The art reports that Endo S is IgG-specific and has no activity for IgA or IgM.[8] The enzyme is commercially available at Genovis AB (IgGZero) and at New England Biolabs (NEB) where the enzyme is tagged with a chitin binding domain (Remove-iT Endo S). Endo S digest is recommended to be carried out in sodium phosphate pH 7.4 (NEB) and over 95% of IgG is described to be deglycosylated within 1 hour. According to the manufacturer NEB, the presence of either a bisecting N-acetylglucosamine and/or alpha-1,6-fucose does not affect the digest. While the enzyme is known in the art to be used to remove N-glycan fragments from IgG, which glycan mixture this enzyme releases from the total mixture of proteins present in human body fluids such as serum has not been reported.

In this disclosure, the term "N-glycans" used is also known in the art as "asparagine-linked glycans," which are present on glycoproteins. The words "glycan" and "sugar" and "carbohydrate" are interchangeable in this disclosure. In addition, a "glycan profile" or a "sugar profile" or a "carbohydrate profile" or "an N-linked glycan profile" or "an N-linked carbohydrate profile" are equivalent terms in this disclosure. In the disclosure, carbohydrates can be digested (or treated, the latter being an equivalent term) with a glycosidase enzyme (e.g., a sialidase to remove the sialic acid residues from the carbohydrates, or a fucosidase to remove fucose residues from the carbohydrates or the Endoglycosidase S). Glycosidase digestions can also be carried out to obtain a more simple profile of the carbohydrates. Sialic acids may also be chemically removed by mild acid hydrolysis of the carbohydrates. In applying the methods of the disclosure, it is less preferred to apply a sialidase digest on the blood, serum or human sample before applying the Endoglycosidase digest on the sample.

Currently, there is no easily measurable and specific serum diagnostic marker for inflammation. In the present disclosure, the possible use of Endo S for measuring the galactosylation of IgG in a human blood, serum or plasma sample was investigated. The need for a reliable, non-invasive diagnostic test that can guide therapeutic decisions in the treatment of inflammation, particularly chronic inflammation, is highly desirable in the art. This disclosure shows that Endo S digestion of human blood, serum or plasma generates a reliable biomarker for measuring the galactosylation of IgG. In addition, the disclosure provides improved methods for measuring the galactosylation of IgG. The improved method is based on the surprising fact that, contrary to the current thinking in the art, Endo S is not IgG specific at the recommended pH of 7.4 but is only IgG specific when Endo S is used in a buffer condition with a pH higher than 7.4, preferably higher than pH 8.0. Under such conditions, the specificity is surprisingly sufficiently high to yield an N-glycan preparation not contaminated with N-glycans derived from other proteins (except specific IgG N-glycans) specific in the total mix of all the different glycoproteins present in a body fluid as complex as human serum. Surprisingly, the released N-glycan fragments form a simpler mixture (or profile) than the one that is derived by PNGase F glycan release from the purified IgG from such body fluids, and the resulting glycan mixture, even when still containing the proteins in this mixture, can then be conveniently analyzed through an optimized method of fluorescent labeling, separation, detection and quantification. From this procedure, biomarkers are derived that determine the IgG galactosylation status and that indicate the inflammatory status of the individual from whom the body fluid sample was taken.

Accordingly, in a first embodiment, the disclosure provides the use of a composition comprising Endoglycosidase S to generate a plurality of N-glycan fragments derived from the total mixture of proteins present in a body fluid derived from a mammal wherein the body fluid consists of blood, serum or plasma, and wherein these released N-glycan fragments are profiled by a glycan analytical technology such as fluorescent labeling, separation by capillary electrophoresis and the N-glycans are then quantified.

In a specific embodiment, the disclosure provides the use of a composition comprising Endoglycosidase S to generate a plurality of N-glycan fragments derived from the total mixture of proteins present in a body fluid derived from a mammal wherein the body fluid consists of blood, serum or plasma and wherein these released N-glycan fragments are profiled by a glycan analytical technology such as fluorescent labeling or separation by capillary electrophoresis. The N-glycans are then quantified, which is carried out without separation (or removal, which is equivalent) of the proteins from the N-glycans. Indeed, after the application of Endoglycosidase S on a body fluid, a heterogeneous mixture is obtained of N-glycan fragments, resulting from the use of Endoglycosidase S, proteins and buffer components.

In a specific embodiment, the use of a composition comprising Endoglycosidase S is carried out at a pH of at least 7.4, at least 7.5, at least 7.6, at least 7.7, at least 7.8, at least 7.9, or at least 8.0.

In a particular embodiment, the use of Endoglycosidase S is carried out at a pH in a range between 7.5 and 8.0.

In yet another specific embodiment, the use is carried out at a pH in a range between 8.0 and 9.0.

In another particular embodiment, the use is carried out at a pH of 8.0.

In another particular embodiment, the use is carried out at a pH of 9.0.

In yet another embodiment, the disclosure provides a method to diagnose or to prognose inflammation in a mammal comprising the following steps: i) digesting the total mixture of proteins present in a body fluid consisting of blood, serum or plasma derived from a mammal with endoglycosidase S, ii) quantifying the galactosylation of the obtained N-glycans (or N-linked carbohydrates) in the profile of carbohydrates obtained, iii) comparing said quantification with profiles from mammals not suffering from inflammation or comparing said quantification with the profile of the same mammal obtained before therapy, iv)

attributing the difference in galactosylation obtained in the previous step with the presence or a prognosis of inflammation.

In this disclosure, the term "mammal" means that the organism can be a human but also animals not limited to domestic animals, such as, for example, a cow, a horse, a dog, a sheep, a goat, or a cat. As such, the methods of the disclosure, such as the diagnostic or prognostic method to diagnose inflammation, can also be applied for veterinary applications.

In the present disclosure, "the comparison of the quantification of galactosylation of N-linked carbohydrates with profiles from mammals not suffering from inflammation" is most conveniently carried out based on the comparison of the quantified galactosylation of N-linked carbohydrates with a previously determined cut-off value for galactosylation. For example, a subject having a lower quantified amount of galactosylation of N-linked carbohydrates present in a body fluid consisting of blood, serum or plasma than the established cut-off value for galactosylation is then diagnosed as suffering from inflammation.

In a particular embodiment, the diagnosis or prognosis of inflammation is chronic inflammation.

In yet another particular embodiment, the diagnosis or prognosis of inflammation is related to the diagnosis or prognosis of non-alcoholic fatty liver disease (NAFLD), non-alcoholic steatohepatitis (NASH), rheumatoid arthritis (RA), osteoarthritis, psoriatic arthritis, ankylosing spondylitis, Crohn's Disease, colitis, ulcerative colitis, and the like.

In yet another embodiment, the disclosure provides a method of diagnosing or prognosing inflammation in a mammal comprising the following steps: i) digesting a body fluid consisting of blood, serum, or plasma with a composition of Endo S having a pH that is at least 7.4, ii) measuring the galactosylation of carbohydrates in the profile obtained, iii) comparing the quantification with profiles from subjects not suffering from inflammation or comparing the quantification with the profile of the same subject obtained before therapy, and iv) attributing the difference in galactosylation obtained in the previous step with the presence or prognosis of inflammation.

In yet another embodiment, the disclosure provides a method of diagnosing or prognosing inflammation in a mammal comprising the following steps:
(i) digesting the total mixture of proteins present in a body fluid consisting of blood, serum or plasma derived from a mammal with Endoglycosidase S to obtain a profile of N-linked glycoforms,
(ii) determining the ratio between at least one agalactosylated glycoform and at least one galactosylated glycoform in the profile,
(iii) attributing at least a more than 5% difference, as compared to the same ratio determined for mammals not suffering from inflammation or the same ratio obtained from mammals suffering from inflammation before receiving therapy, with the presence or prognosis of inflammation.

In yet another embodiment, the disclosure provides a method of diagnosing or prognosing inflammation in a mammal comprising the following steps:
(i) digesting the total mixture of proteins present in a body fluid consisting of blood, serum or plasma derived from a mammal with Endoglycosidase S to obtain a profile of N-linked glycoforms,
(ii) determining the ratio between at least one agalactosylated glycoform and at least one galactosylated glycoform in the profile,
(iii) attributing at least a more than 5% difference, at least more than 10% difference, at least more than 15% difference, at least more than 20% difference, at least more than 25% difference, at least more than 30% difference, at least more than 35% difference, at least more than 40% difference, at least more than 45% difference, at least more than 50% difference, at least more than 55% difference, at least more than 60% difference, at least more than 65% difference, at least more than 70% difference, or at least more than 75% difference, as compared to the same ratio determined for mammals not suffering from inflammation or the same ratio obtained from mammals suffering from inflammation before receiving therapy, with the presence or prognosis of inflammation.

In a specific embodiment, the method of diagnosing or prognosing inflammation in a mammal is used to diagnose or prognose NASH in a mammal.

In a specific embodiment, the method of diagnosing or prognosing inflammation in a mammal is carried out with the use of Endoglycosidase S at a pH higher than 7.4.

In another specific embodiment, the method of diagnosing or prognosing inflammation in a mammal is carried out with the use of Endoglycosidase S at a pH higher than 7.5, higher than 7.6, higher than 7.7, higher than 7.8, higher than 7.9, higher than 8.0.

In a specific embodiment, the method of diagnosing or prognosing inflammation in a mammal is carried out with the use of Endoglycosidase S at a pH ranging between 7.5 and 9.0.

In another specific embodiment, the method of diagnosing or prognosing inflammation in a mammal is carried out with the use of Endoglycosidase S at a pH ranging between 8.0 and 8.5.

In yet another specific embodiment, the method of diagnosing or prognosing inflammation in a mammal is carried out with the use of Endoglycosidase S at a pH ranging between 8.0 and 9.0.

In yet another specific embodiment, the method of diagnosing or prognosing inflammation in a mammal is carried out with the use of Endoglycosidase S at a pH ranging between 8.5 and 9.0.

The wording "measuring the galactosylation of carbohydrates" is equivalent to the wording "measuring the a-galactosylation of carbohydrates." Indeed, it is known in the art that a lower galactosylation of IgG occurs in inflammatory conditions, particularly chronic inflammatory conditions. Non-limiting examples of chronic inflammatory conditions are, for example, rheumatoid arthritis (RA), inflammatory bowel disease (IBD), tuberculosis, ankylosing spondylitis (AS), and chronic liver disease.

The wording "quantifying the galactosylation" means that in an inflammatory condition, particularly a chronic inflammatory condition, the galactosylation of IgG proteins (i.e., the presence of galactose sugar groups on the N-linked glycans of IgG) is less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, or even less than the level of galactosylation of IgG proteins in a non-inflammatory condition.

In a specific embodiment, the disclosure provides a biomarker (in the examples below defined as "UGS4") for measuring the galactosylation of carbohydrates on IgG in a blood, serum or plasma sample derived from a patient, which biomarker is calculated as:

$$UGS\ 4 = \frac{(2*(NGA2F^*)) + (NG1A2F\_1^* + NG1A2F\_2^*)}{(2*(NGA2F^* + NG1A2F\_1^* + NG1A2F\_2^* + NA2F^*))}$$

Figure 11:
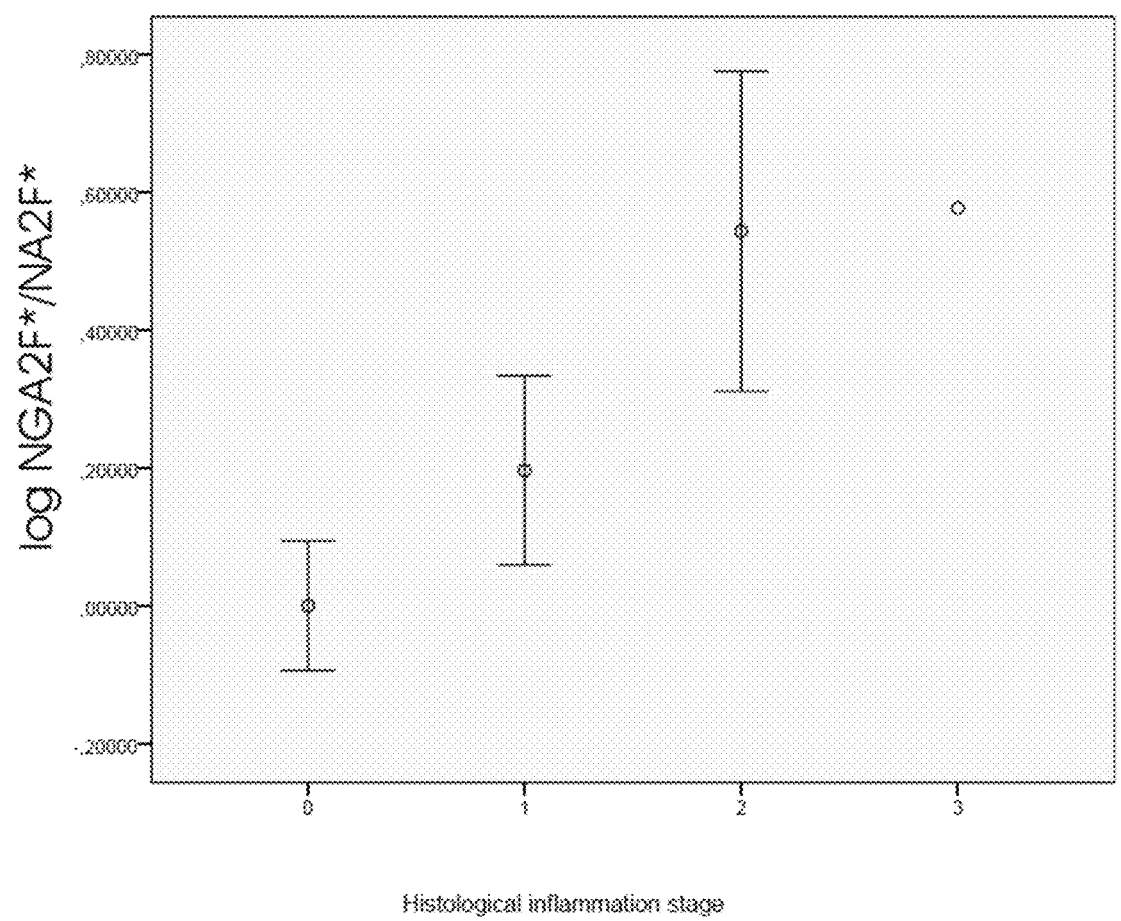
FIG. 11: Serum samples from 49 patients were processed with Endo S and the glycan profiles were quantified. A simple undergalactosylation score based on the log-transformed ratio between the peak height of the fully agalactosylated glycan NGA2F* and the fully galactosylated glycan NA2F* was calculated and plotted vs. the histologically determined lobular inflammation stage. Error bars indicate the 95% confidence interval for the mean. (n=27 for inflammation stage 0, n=16 for stage 1, n=5 for stage 2 and n=1 for stage 3.)
Figure 12:
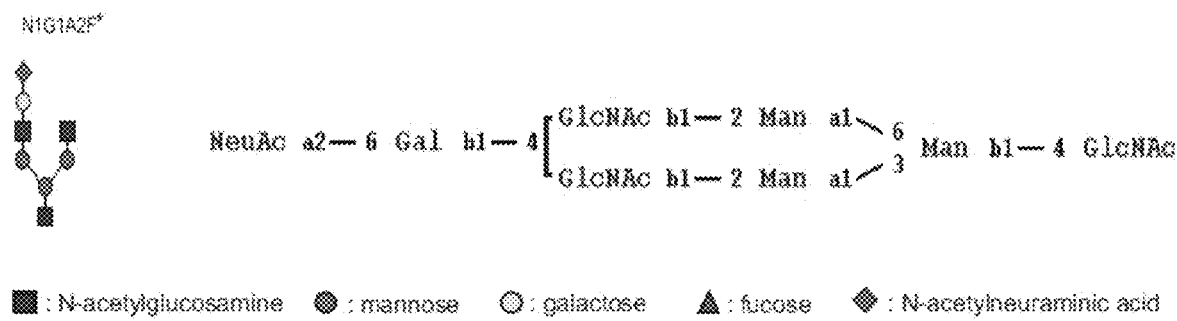
FIG. 12: The glycan structure and the name of the name of the IUPAC 2D representation of the glycan of the condensed N-glycan nomenclature NeuAc(α-2,6)Gal(β-1,4) GlcNAc(β-1,2)Man(α-1,3)[GlcNAc(β-1,2)Man(α-1,6)] Man(β-1,4)GlcNAc. Please note that this structure represents two isomers since the sialic acid-galactose (SA-GAL) can be present on one of the two arms.
Figure 13:
FIG. 13: The glycan structure and the name of the name of the IUPAC 2D representation of the glycan of the condensed N-glycan nomenclature NeuAc(α-2,6)Gal(β-1,4) GlcNAc(β-1,2)Man(α-1,3)[Gal(β-1,4)GlcNAc(β-1,2)Man (α-1,6)]Man(β-1,4)GlcNAc. Please note that this structure represents two isomers since the sialic acid (SA) can be present on one of the two arms.
Figure 14:
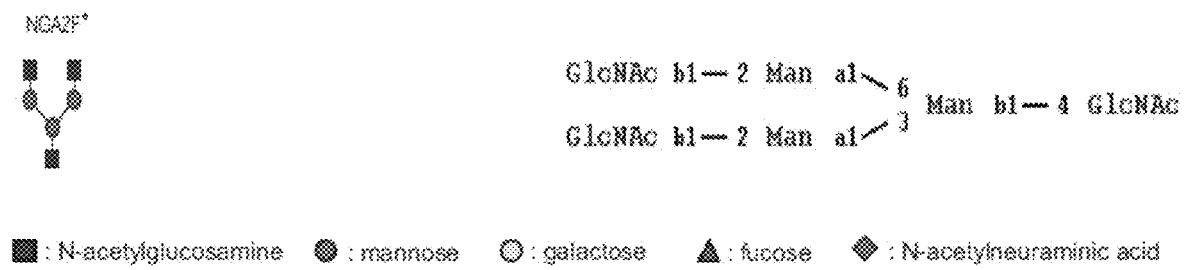
FIG. 14: The glycan structure and the name of the name of the IUPAC 2D representation of the glycan of the condensed N-glycan nomenclature GlcNAc(β-1,2)Man(α-1,3)[GlcNAc(β-1,2)Man(α-1,6)]Man(β3-1,4)GlcNAc.
Figure 15:
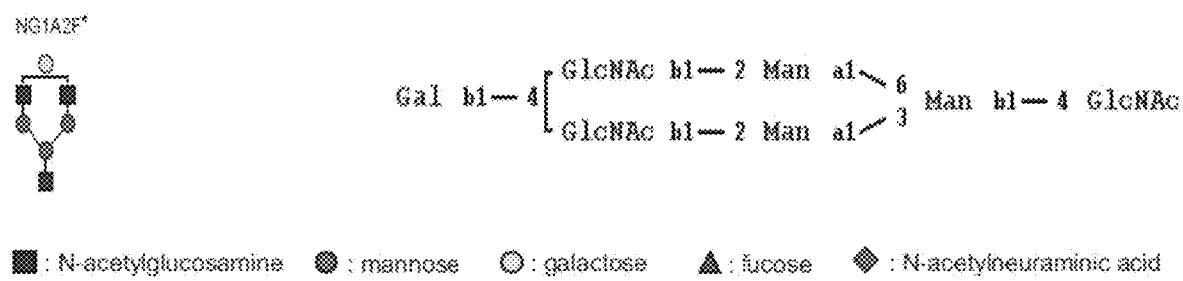
FIG. 15: The glycan structure and the name of the name of the IUPAC 2D representation of the glycan of the condensed N-glycan nomenclature Gal(β3-1,4)GlcNAc(β-1,2)Man(α-1,3)[GlcNAc(β-1,2)Man(α-1,6)]Man(β-1,4) GlcNAc. Please note that this structure represents two isomers since the galactose (GAL) can be present on one of the two arms, represented as NG1A2F_1* and NG1A2F_2*.
Figure 16:
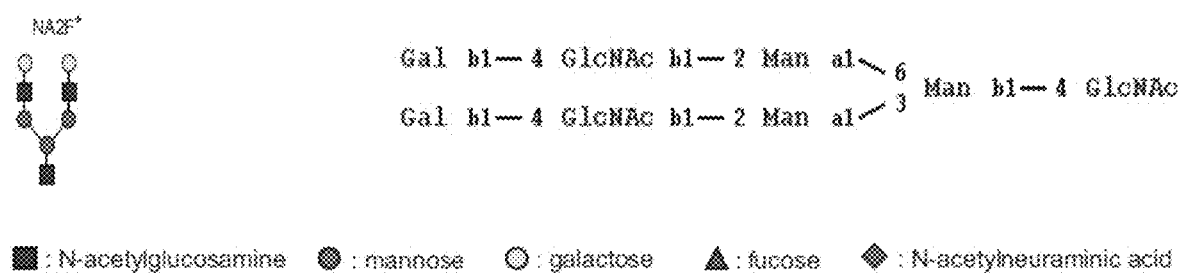
FIG. 16: The glycan structure and the name of the name of the IUPAC 2D representation of the glycan of the condensed N-glycan nomenclature Gal(β-1,4)GlcNAc(β-1,2)Man(α-1,3)[Gal(β-1,4)GlcNAc(β-1,2)Man(α-1,6)]Man (β-1,4)GlcNAc.

In another specific embodiment, the disclosure provides a specific biomarker for measuring the galactosylation of carbohydrates on IgG in a blood, serum or serum sample derived from a patient, which biomarker is calculated as the ratio between NGA2F* and NA2F*. The experimental data, the latter biomarker correlates perfectly with UGS4, which is a biomarker more complex to calculate. With respect to the ratio of the two specific biomarkers (NGA2F* and NA2F*), it is convincingly shown in FIG. 11 that the higher the log ratio between NGA2F* and NA2F*, the higher the inflammation score. In the diagnostic method utilized, a ratio of 5% was calculated to be easily distinguished between two different body samples.

The abbreviated names of the structures digested by Endo S applied on serum, plasma or blood (as used hereinbelow), as well the glycan-structure, the name of the IUPAC 2D representation and the condensed N-glycan nomenclature are depicted in FIGS. 12-16.

In yet another embodiment, the disclosure provides a kit for measuring or prognosticating inflammation, the kit comprising a composition of Endo S wherein the pH of the composition is at least 7.4, buffers and reagents for quantifying galactosylation of carbohydrates.

In a particular embodiment, the method of the disclosure can be used for monitoring the effect of therapy administered to a human suffering from inflammation, particularly chronic inflammation. In another particular embodiment, the method of the disclosure specifically detects inflammation, particularly chronic inflammation. The term "specifically" refers to the fact that inflammation can be diagnosed differently from other disorders comprising humans suffering from cancer or infection. It is expected that when the therapy is successful, that the galactosylation of the IgG molecules increases. The methods of the disclosure provide a quantitative determination of the galactosylation of the IgG molecules present in a patient's blood, serum or plasma sample.

Figure 8:
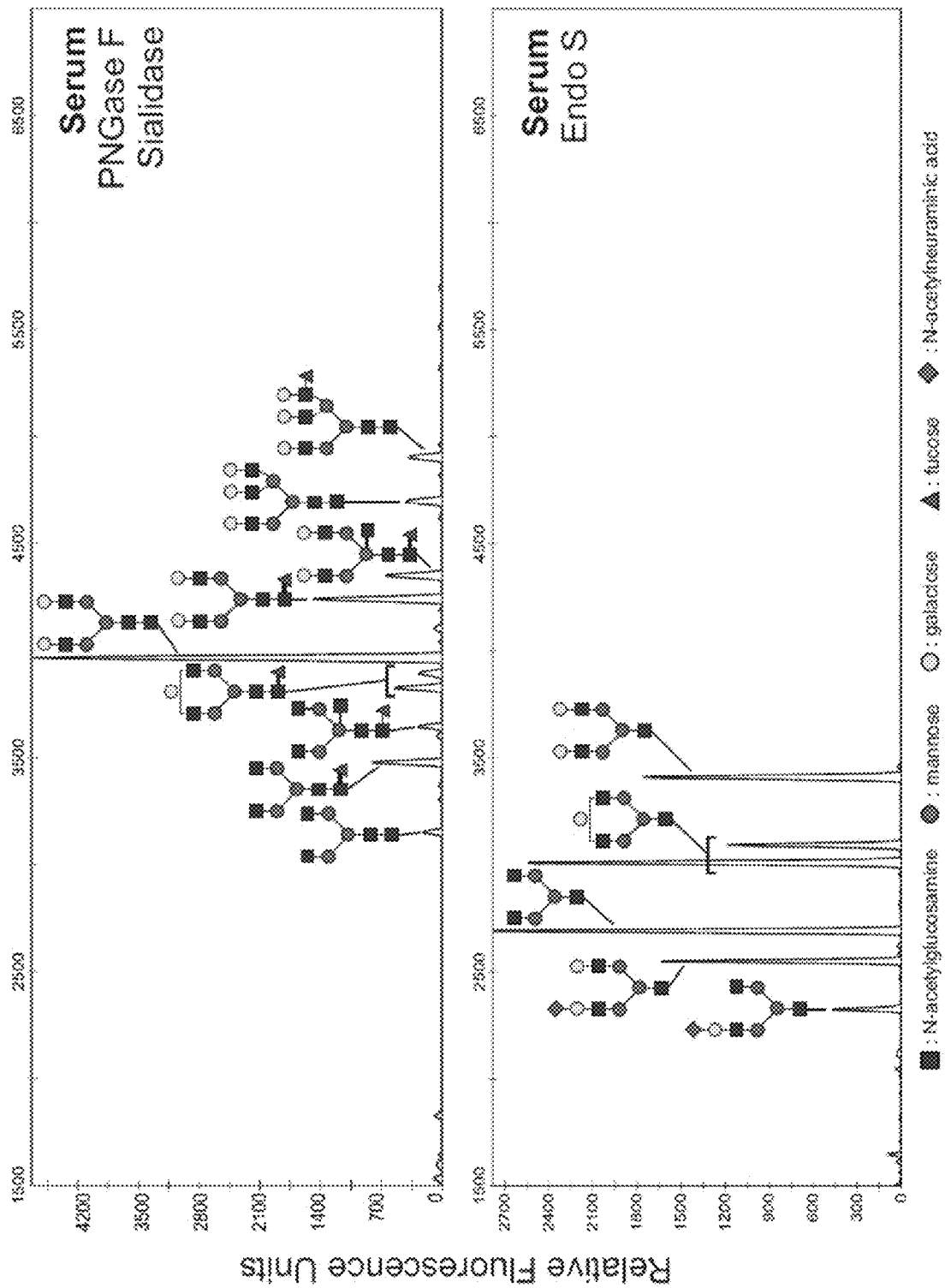
FIG. 8: Comparison between an Endo S digestion of a human serum sample (lower panel) with respect to a PNGase F digestion of the same human serum sample (upper panel).

The wording "a profile of carbohydrates" means any entity comprising qualitative and/or quantitative information on the carbohydrates. For example, this may mean an electrophoretic or chromatographic profile of the carbohydrates. In a particular case, the profile is a mass spectrum of the carbohydrates. Alternatively, the profile can be information obtained by Nuclear Magnetic Resonance analysis. In yet another example, the profile can be information describing qualitative or quantitative aspects of lectin binding to the carbohydrates. Alternatively, the profile can be information describing the extent to which the carbohydrates are substrates for specific enzymes such as glycosyltransferases or glycosidases. Such information can include read-outs of measurements of by-products of such enzymatic reactions, such as nucleotides set free in equimolar amounts in glycosyltransferase reactions. In a particular embodiment, the wording "generating a profile of carbohydrates" or "profiling of carbohydrates" also can imply that the glycan structures are separated and subsequently detected. Usually, a number of carbohydrates are identified in a profile of carbohydrates. In the methods of the disclosure, a typical Endo S digest on a human sample consisting of human serum generates six different glycan structures in the profile (see, FIG. 8, lower panel). In comparison, a PNGase F digest on human serum leads to a profile with a completely different profile (see, FIG. 8, upper panel). Usually, the carbohydrates are present in a complex mixture and separation is necessary for an efficient detection. Separation can be carried out with methods comprising electrophoretic and chromatographic methods. Detection can be carried out with methods comprising antibody detection, lectin detection, NMR, mass spectrometry and fluorescence. In a particular embodiment, it is necessary to chemically and/or enzymatically remove the glycans from the glycoproteins before the glycans can be profiled. Methods of preparing glycans from glycoproteins are well known in the art. In another particular embodiment, it is necessary to derivatize the glycans before the separation and the detection. In one approach of the method of this disclosure, the profiling (including separation and detection) of glycans can be carried out in combination with, for example, a DNA-sequencing device. However, it is clear for the person skilled in the art that this method can also be applied in connection with capillary electrophoresis (CE) systems adaptable to a laser-induced fluorescence detector. Such systems, for instance, include the P/ACE series Capillary Electrophoresis Systems (Beckman Instruments, Inc., Fullerton, Calif.). The disclosure can also be applied with any electrophoresis system that is adaptable with either a laser, light-emitting diode (e.g., 2100 Bioanalyzer from Agilent and MultiNA from Shimadzu) or deuterium lamp (e.g., V8 analyzer from Helena Biosciences) in conjunction with suitable detectors. In another embodiment, mass spectrometric detection methods can also be used such as MALDI-TOF-MS for the measurement of the amount of at least one carbohydrate or a fragment derived thereof. In mass spectrometric methods, very often the carbohydrates are fragmented and, therefore, in the methods, fragments of carbohydrates are detected.

In yet another embodiment, the profiling can be carried out with a microfluidics method. Microfluidics is a rapidly growing field and is based on fluid migration through narrow-bore channels created in a solid medium (mostly silica wafers or high-purity glass plates) via techniques borrowed from the microchip industry (photolithography and chemical wet etching). Fluids can migrate through these channels via capillary action or active pumping, and analytes can migrate in fluid-filled channels through electrophoresis (Schmalzing et al. (2001), *Methods Mol. Biol.* 163, 163-173). In yet another embodiment, the separation of carbohydrates can be carried out via a chromatographic separation with methods including thin layer chromatography (TLC), high performance liquid chromatography, gas chromatography and high performance anion-exchange chromatography.

The term "labeled derivatives of carbohydrates" or "labeling of carbohydrates" refers to carbohydrates that have been labeled with an agent that leads to an efficient detection of the carbohydrates. Labeled carbohydrates are also called derivatized carbohydrates. As an example, a fluorescing compound can be used for the labeling of the carbohydrates. Fluorescing compounds are also preferentially charged such that the derivatized compounds can migrate under electrophoretic conditions. When the fluorophore label is uncharged, it can be coupled with a charge imparting species. The fluorophore label also permits the quantitative measurement of the derivatized carbohydrates by fluorescence. Fluorescing compounds such as 9-aminopyrene-1,4,6-trisulfonic acid (APTS) and 8-aminonaphthalene-1,3,6-trisulfonic acid (ANTS) are particularly suitable for electrophoretic separation of derivatized carbohydrates. Other compounds for fluorescent labeling of carbohydrates include 2-aminopyridine (AP), 5-aminonaphthalene-2-sulfonate (ANA), 1-amino-4-napthalene sulfonic acid (ANSA), 1-amino-6,8-disulphonic acid (ANDA), 3-(4-carboxybenzoyl)-2-quinolinecarboxaldehyde (CBQCA), lucifer yellow, 2-aminoacridone and 4-aminobenzonitrile (ABN).

In a particular embodiment, regarding the detection of the fluorescently labeled carbohydrates, any detection method known in the art can be applied, but preferably the detection is carried out with a laser such as a diode laser, a He/Cd laser or an argon-ion laser. In a particular embodiment, the profile of labeled carbohydrate bands produced by the electrophoretic separation is visualized using an imaging system based on a charge-coupled device (CCD) camera. Information from the CCD camera may subsequently be stored in digital form and analyzed by various computer programs for comparing diagnostic carbohydrate patterns between individuals and between reference standards. In another particular embodiment, the gel separated diagnostic carbohydrates may be transferred to an immobilizing membrane, i.e., blotted and then probed with various diagnostic carbohydrate-specific reagents such as lectins or monoclonal or polyclonal antibodies specific for the diagnostic carbohydrates. Ligands comprise lectins and antibodies. For example, the increased abundance of the N-glycan structures (or their conjugates) with a "bisecting GlcNAc" residue (GnT-III product) in a body fluid sample can be detected with a lectin that specifically recognizes glycans (or their conjugates) that are modified with a bisecting GlcNAc, such as the erythro-agglutinating lectin from *Phaseolus vulgaris* (E-PHA). Alternatively, the increased abundance of the N-glycan structures with a "bisecting GlcNAc" residue (or their conjugates) can be detected by a reduction in the binding to the N-glycans (or their conjugates) to lectins that only bind N-glycans (or their conjugates) if they are not substituted with a bisecting GlcNAc residue. An example of such a lectin is the lectin from *Canavalia ensiformis* (Con A). The observed undergalactosylation of the serum glycoprotein N-glycans can be detected by a terminal-GlcNAc binding lectin such as the *Griffonia simplicifolia* II (GS-II) lectin. Alternatively, the undergalactosylation can be measured by a reduction in the binding of a terminal-galactose binding lectin such as the lectin from *Erythrina crystagalli*.

In a particular embodiment, the glycosylation profile obtained after Endo S digestion of a human blood, serum or plasma sample can be analyzed by measuring the property of the carbohydrates that is constituted of being a substrate for a specific glycosyltransferase. In a preferred embodiment, this glycosyltransferase is beta-1,4-galactosyltransferase. An additional substrate for this reaction is UDP-Galactose, and the reaction yields UDP in a stoichiometric amount. Thus, the profile can be analyzed by measuring the difference between the extent of galactosylation of the proteins before and after the reaction, for example, by a method involving binding of the glycoproteins to a lectin specific for terminal beta-galactose (such as the lectins known in the art derived from *Ricinus communis* and from *Erythrina crystagalli*, or the galectins such as the one derived from *Coprinus cinereus*). Alternatively, the profile can be obtained by measuring the amount of UDP generated in the beta-1,4-galactosyltransferase reaction on the mixture of blood, serum or plasma proteins, for example, by HPLC. The amount of UDP can also be measured using a coupled enzyme reaction with one or more enzymes known from nucleotide metabolism, such as, for example, a nucleotide diphosphatase such as the yeast Golgi GDPase, which also shows significant hydrolytic activity toward UDP. In this latter case, the profile can be obtained by measuring either UMP or phosphate, using well-known techniques. Still another example of a measurement of UDP involves the use of supramolecular membrane pores with differential affinity for UDP-Gal and UDP, as known in the art. The profiles thus obtained can, for example, be standardized for the total amount of protein or carbohydrate present in the blood, serum or plasma sample.

In another embodiment, the carbohydrate profiling method can be supplemented pre-electrophoretically with one or more internal standards labeled with a chromophore or fluorophore, which is either different or the same as the label attached to the carbohydrate analytes. The internal standard allows for accurate and reproducible determination of the electrophoretic mobilities of the derivatized carbohydrate by referencing these mobilities to the mobilities of the components in the internal standard mixture. The internal standards could be sugars or other macromolecules including DNA. For example, a LIZ-labeled oligonucleotide standard Genescan™ 500 (Applied Biosystems, Foster City, Calif., USA) or a mixture of rhodamine-labeled 6-, 18-, 30-, and 42-meric oligonucleotides may be added to the derivatized glycans before profiling. Diagnostics standards may be labeled prior to the labeling of the samples for analysis; however, diagnostic standards are preferably labeled concomitantly with the labeling for the standards for analysis. Furthermore, the diagnostic carbohydrates in the standards are preferably quantitated so as to provide for quantitative or qualitative comparisons with the amount of diagnostic carbohydrates in the samples for analysis.

The term "body fluid" includes blood, blood serum and blood plasma. Preferred body fluids for analysis are those that are conveniently obtained from mammals such as a human patient. Particularly preferred body fluids include blood serum and blood plasma.

Although this disclosure can be carried out without pre-treatment of the sample prior to the profiling of the (derivatized) glycans in a particular embodiment, samples for analysis may be processed prior to the separation and quantification of the diagnostic carbohydrates. The precise method of sample processing employed may vary in accordance with a number of factors attributable to the choice of sample fluid and the identity of the diagnostic carbohydrates. These factors include: the abundance of the diagnostic carbohydrate, the concentration of background carbohydrates, the presence of interfering molecules, for example, molecules that adversely affect diagnostic carbohydrate band mobility or the fluorescent labeling of the diagnostic carbohydrates, and whether the fluorescent label has to be separated from the derivatized diagnostic carbohydrates. Suitable methods for this processing or pre-treatment of samples include: dialysis, to remove interfering molecules (e.g., salt for an efficient mass spectrometric detection); ultrafiltration, to concentrate diagnostic carbohydrates and remove interfering molecules; centrifugation, to remove interfering particulates or concentrate cells; precipitation, to remove interfering molecules, removal of albumin from the serum to enrich for glycosylated proteins and, hence, for lower abundance glycans, to generate a more simple glycan profile; chromatography such as affinity chromatography to remove, for example, albumin from the serum.

In another embodiment of the disclosure, in order to be able to measure relative amounts of the carbohydrates, diagnostic standards are used to analyze the diagnostic carbohydrates in the mammal samples; however, the information embodied by the diagnostic standard, e.g., migration distance and intensity, may also be obtained from comparison with stored records made from diagnostic standards previously subjected to fluorophore-assisted carbohydrate electrophoresis under conditions similar to the conditions to which the samples for analysis are exposed. Diagnostic standards may be both positive, i.e., corresponding to the complete carbohydrate pattern in an afflicted individual, or negative, i.e., corresponding to an unafflicted individual. Diagnostic standards may have a composition similar to that of samples for analysis in that they may contain both diagnostic carbohydrates and background carbohydrates with compositions similar to that found in actual samples. Diagnostic standards may be derived from samples obtained from afflicted and non-afflicted individuals. Alternatively, diagnostic standards may contain one or more diagnostic carbohydrates free of background carbohydrates.

In another embodiment, the disclosure also includes a kit for performing diagnosis of inflammation, particularly chronic inflammation. For example, a kit can be made for performing fluorophore-assisted carbohydrate electrophoresis diagnosis of chronic inflammation. As another example, a kit can be made for performing mass spectrometric diagnosis of chronic inflammation. Fluorophore-assisted carbohydrate electrophoresis diagnosis kits provide collections of reagents required for performing the diagnosis of chronic inflammation. Suitable kits enable laboratories to conveniently perform fluorophore-assisted carbohydrate electrophoresis diagnosis. Kits may include reagents for performing tests to identify chronic inflammation. Kits may include diagnostic standards, fluorescent label, blotting and binding materials, e.g., membranes, carbohydrate specific binding reagents, lectins, instructions, sample containers, and polyacrylamide gel reagents, precast gels, enzyme buffers, reducing agents (for use in the fluorophore labeling of carbohydrates), and glycosidase enzymes (e.g., sialidase, galactosidase, fucosidase) capable of catalyzing reactions that structurally alter diagnostic carbohydrates. More complete kits may include equipment for performing fluorophore-assisted carbohydrate electrophoresis, such as polyacrylamide gel apparatus, CCDs, laser, DNA sequencer, computers, software, and the like. Reagents included in fluorophore-assisted carbohydrate electrophoresis diagnosis kits are preferably provided in pre-measured amounts. The kits preferably include the instructions for carrying out the fluorophore-assisted carbohydrate electrophoresis method of this disclosure.

In a specific embodiment, the disclosure provides a diagnostic kit for detecting or prognosing inflammation in a subject wherein the kit comprises buffers, Endoglycosidase S and the two reference glycans NGA2F* and NA2F*.

The diagnostic test is useful in practice because it is sufficiently easy to apply on a large scale by normally trained laboratory staff. Furthermore, since electrophoresis-based high-resolution and high-sensitivity analyzers for DNA sequencing and mutation detection are already present in a rapidly increasing number of clinical laboratories or are affordable for most clinical laboratories, the novel diagnostic glycomics test for chronic inflammation can be run on them. Moreover, the available range of DNA analyzers allows for the sample throughput to be easily scaled from just a few to hundreds of samples per day per machine, depending on the demand of each laboratory. This DNA-analysis equipment offers the added advantage of automation, reducing the complexity of the overall analytical process. Alternatively, the diagnostic glycomics test could also be applied on cheap CE-based microfluidics instruments, such as the 2100 Bioanalyzer or MultiNA, which are the current standard in molecular biology research laboratories. In another embodiment, the method for the detection of chronic inflammation further comprises clinical chemistry parameters. Thus, the disclosure can also be conveniently carried out in combination with clinical chemistry parameters and/or imaging parameters. Measurement of clinical chemistry parameters comprises measurement of levels of CRP and the sedimentation rate of the red blood cells. Imaging comprises ultrasound, CT-scan and MRI-scan.

It is to be understood that although particular embodiments, specific configurations, as well as materials and/or molecules, have been discussed herein for methods according to this disclosure, various changes or modifications in form and detail may be made without departing from the scope and spirit of this disclosure. The following examples are provided to better illustrate particular embodiments, and they should not be considered limiting the application. The application is limited only by the claims.

Examples

Figure 1B:
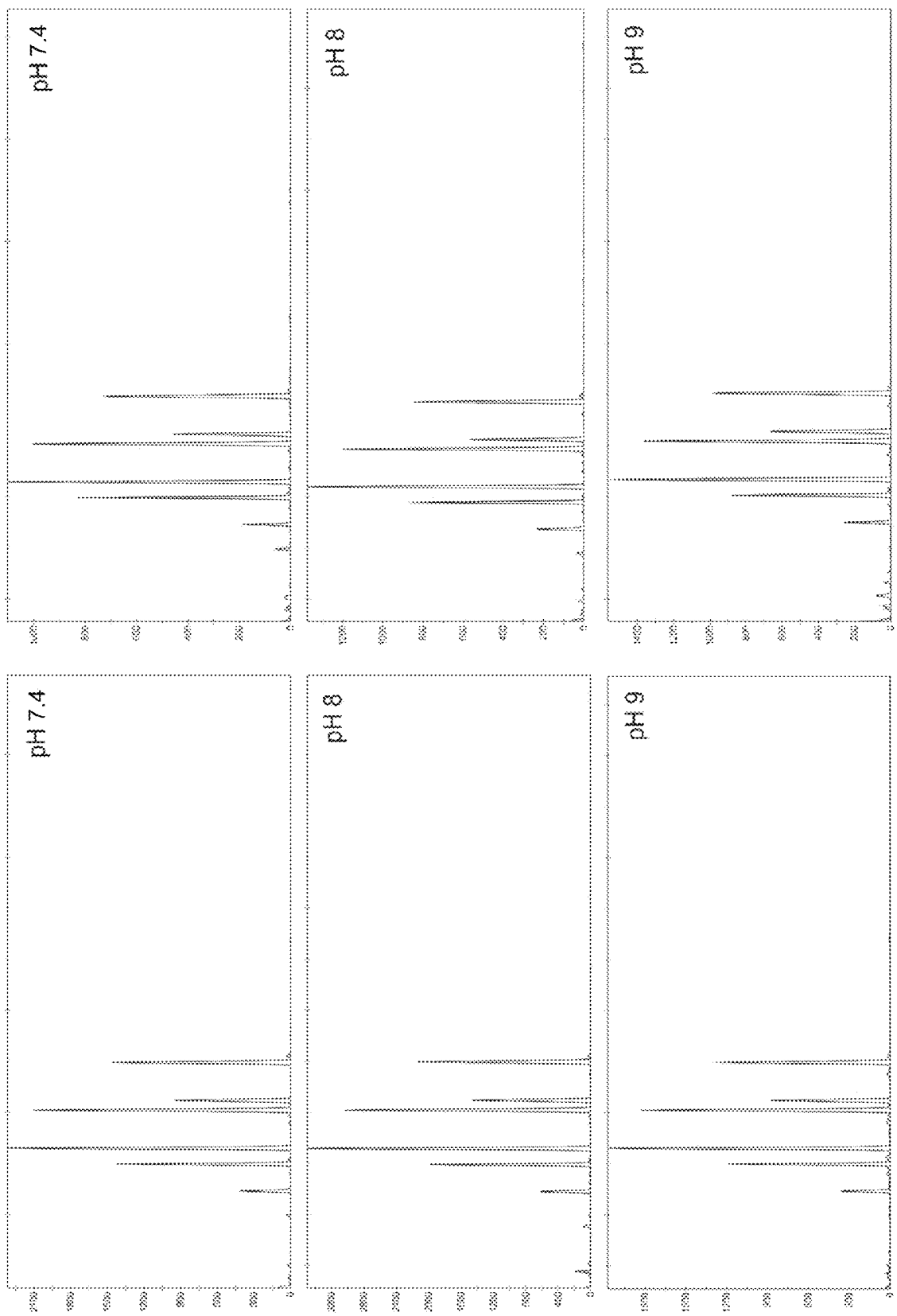

1. Endoglycosidase S is Only IgG Specific at a pH Higher than 8.0 in the Presence of IgA and IgM Immunoglobulins It is taught in the art that Endoglycosidase S (Endo S) is IgG specific and manufacturers recommend the use of Endo S at pH 7.4. However, in the present example, it is shown that Endo S can also cleave sugars from IgA and IgM at the recommended pH. Remarkably, this non-specific cleavage is more pronounced at a lower pH and is almost completely absent at pH 8 or higher. Reaction conditions at different pH conditions (pH 5, pH 6, pH 7.4, pH 8 and pH 9) were carried out on purified IgG in the presence of Endo S and compared to an Endo S digestion on a mixture of IgG, IgA and IgM. After the Endo S cleavage reaction, the released sugars were dried and labeled with APTS. After 2×SEC clean-up, the labeled samples were analyzed on a DNA-sequencer. FIGS. 1A and 1B depict an Endo S digest on pure IgG and it is seen that very similar profiles are obtained at the five different pH conditions. Only small differences in ratios of the different peaks are visible at pH 5 but this is due to an inefficient digestion of carbohydrates at the lowest pH (pH 5). The latter was confirmed by on-membrane deglycosylation. Thereto, the Endo S-treated IgG was bound to a PVDF membrane and the remaining N-glycans (i.e., the glycans that were unaffected by Endo S) were cleaved with Peptide N-glycosidase F (PNGase F). An important observation was that the relative abundances of each N-glycan remained constant at different pH conditions. FIGS. 1A and 1B show the differences (in red) in the profiles between pure IgG and the IgG, IgA, IgM mix. Unexpectedly, in the lower pH range, non-specific cleavage of IgA and IgM occurs. In particular, a bisialylated structure appearing in the carbohydrate profile and a monosialylated structure that was increasing was observed. Importantly, the non-specific cleavage decreases with increasing pH. At pH 8 only very limited differences in Endo S digestion between pure IgG and the IgG, IgA, IgM mix are present. At pH 9, no aspecific cleavage of Endo S occurs anymore.

2. Endo S is Only Fully IgG-Specific in Human Serum at a pH Higher than 8.0

Figure 2A:
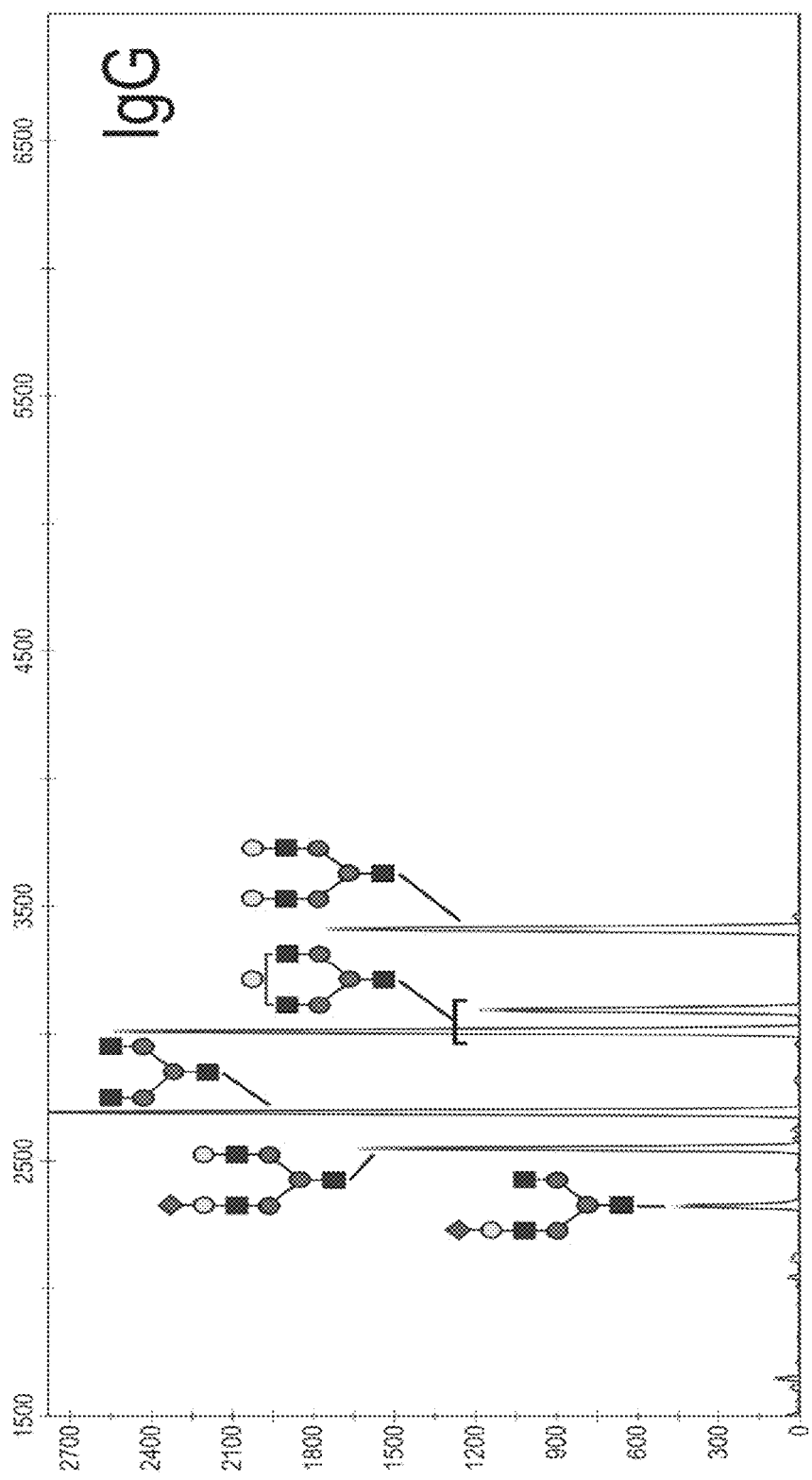
FIGS. 2A-2C: Endo S digest on IgG-depleted serum to which purified IgG was added (left panel) or not (right panel). Each (fraction of) peak marked in red represents glycans derived from non-IgG glycoproteins.
Figure 2B:
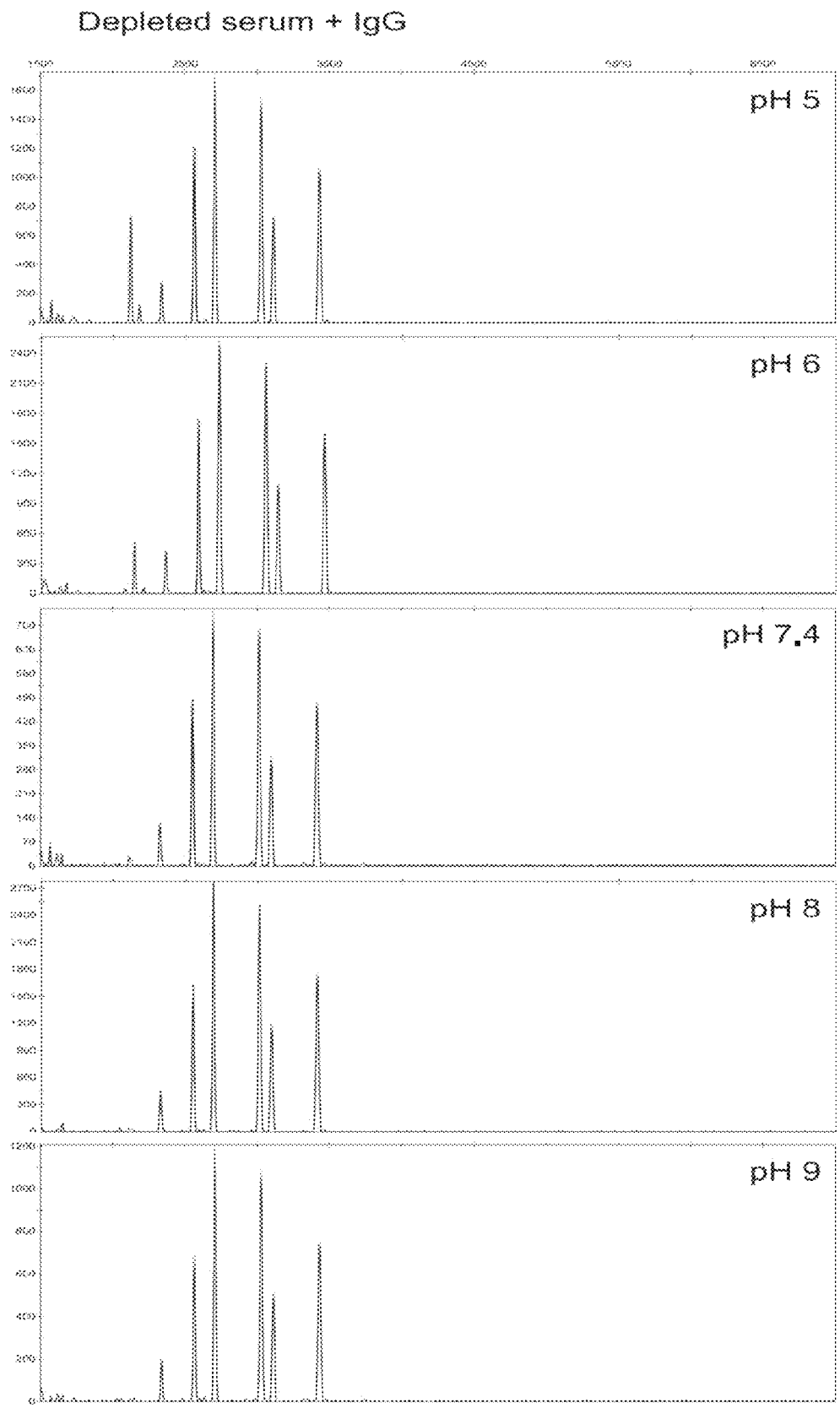
Figure 2C:
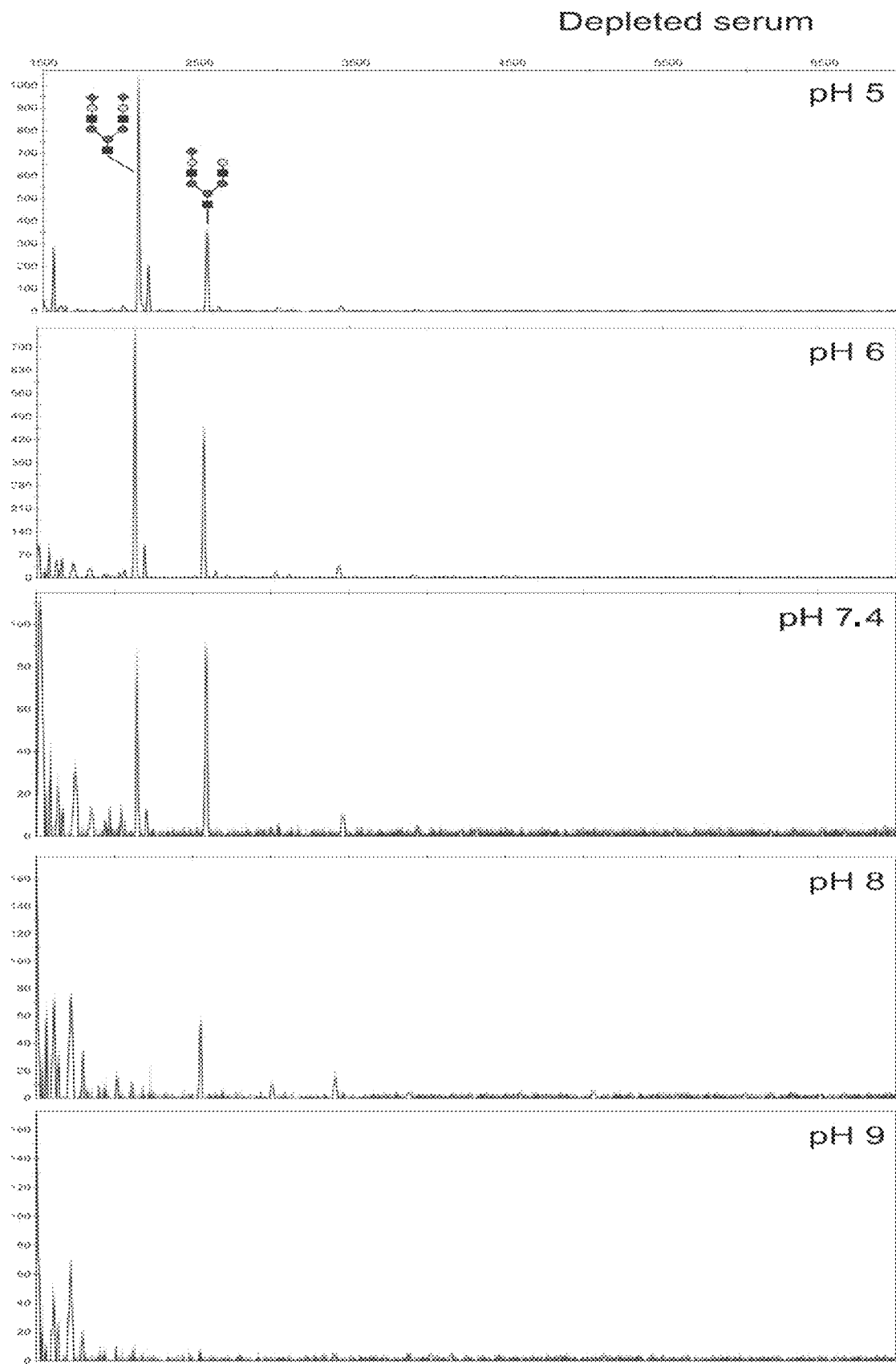

In human serum, it was observed that Endo S can cleave bisialylated and monosialylated glycan structures from serum proteins different than the reported IgG proteins. Currently, it is unknown which proteins are deglycosylated but IgA and/or IgM are suspected to be cleaved as well. This non-specific cleavage is more pronounced at a lower pH and is almost completely absent at a pH higher than 8.0. In the present example, serum was prepared from fresh blood. IgG was depleted from the serum using the PROTEOPREP® Immunoaffinity Albumin & IgG Depletion Kit. The depletion was confirmed by SDS-PAGE and Western Blot (>99% of IgG was removed). Subsequently, Endo S was added to the depleted serum under different pH conditions. In a second set of samples, commercial IgG was added to the depleted serum before carrying out an Endo S digest again under different pH-conditions. FIGS. 2A-2C show the Endo S profile of pure IgG compared with the serum samples. Red peaks show non-specific cleaving by Endo S derived from glycans from proteins other than IgG. In the depleted serum, a bisialylated and a monosialylated structure are present. Remarkably, the presence of these sialylated glycan structures decreases with increasing pH. The bisialylated structure is completely absent at pH 8.0 and the monosialylated structure is only present in the background. IgG-depleted serum to which commercial IgG was added shows the same sugar profile as pure IgG starting from pH 8.0. It is concluded that Endo S is only IgG-specific in serum starting from pH 8 and higher.

Figure 3A:
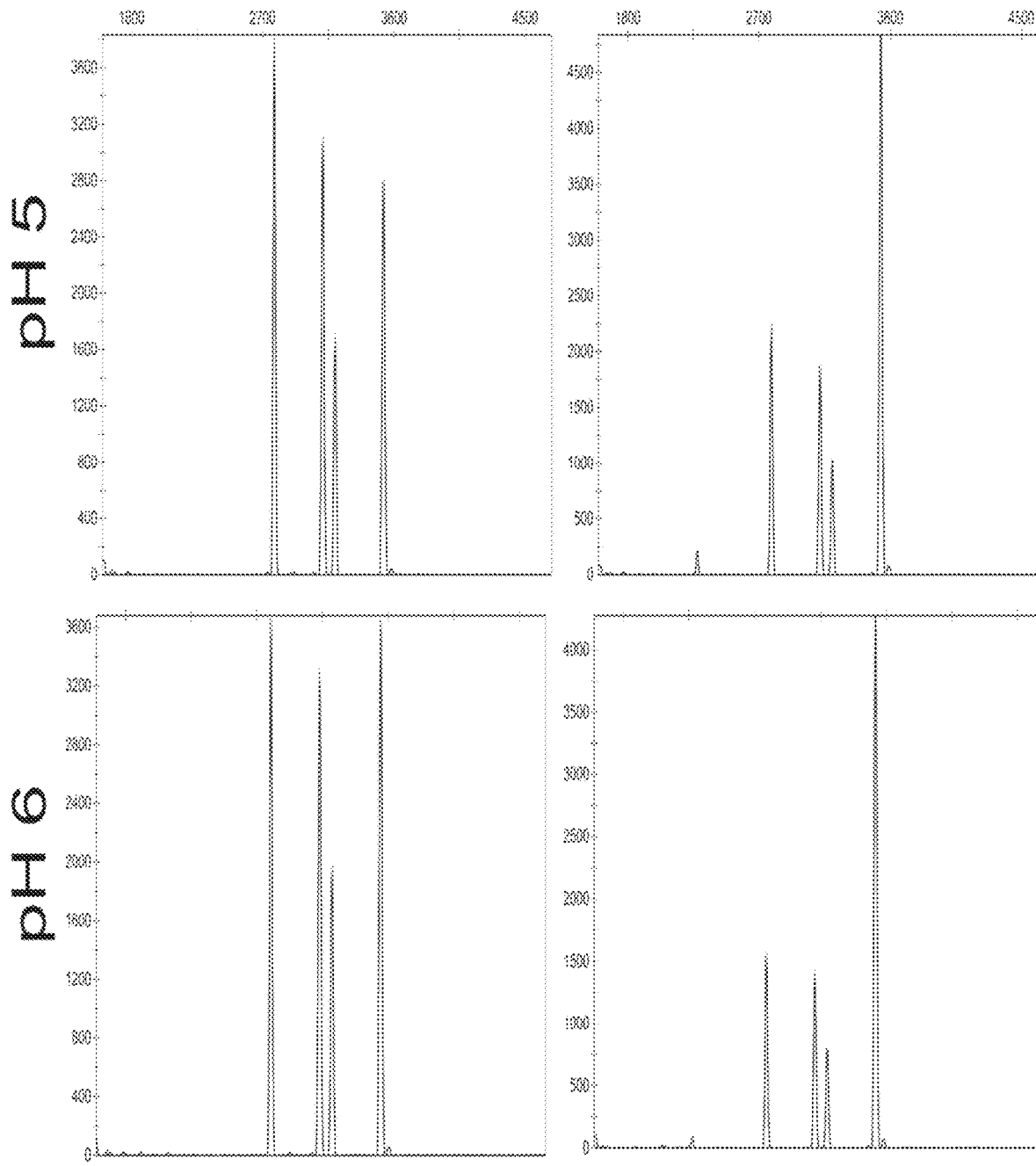
FIGS. 3A and 3B: Endo S digest on IgG (left panel) and IgG, IgA and IgM mixture (right panel) after sialidase treatment. N-glycan profile obtained after Endo S digest of desialylated IgG is independent of the pH during the digestion. In contrast, a different profile for each tested pH is the result of a specific cleavage of desialylated sugars from other antibody classes.
Figure 3B:
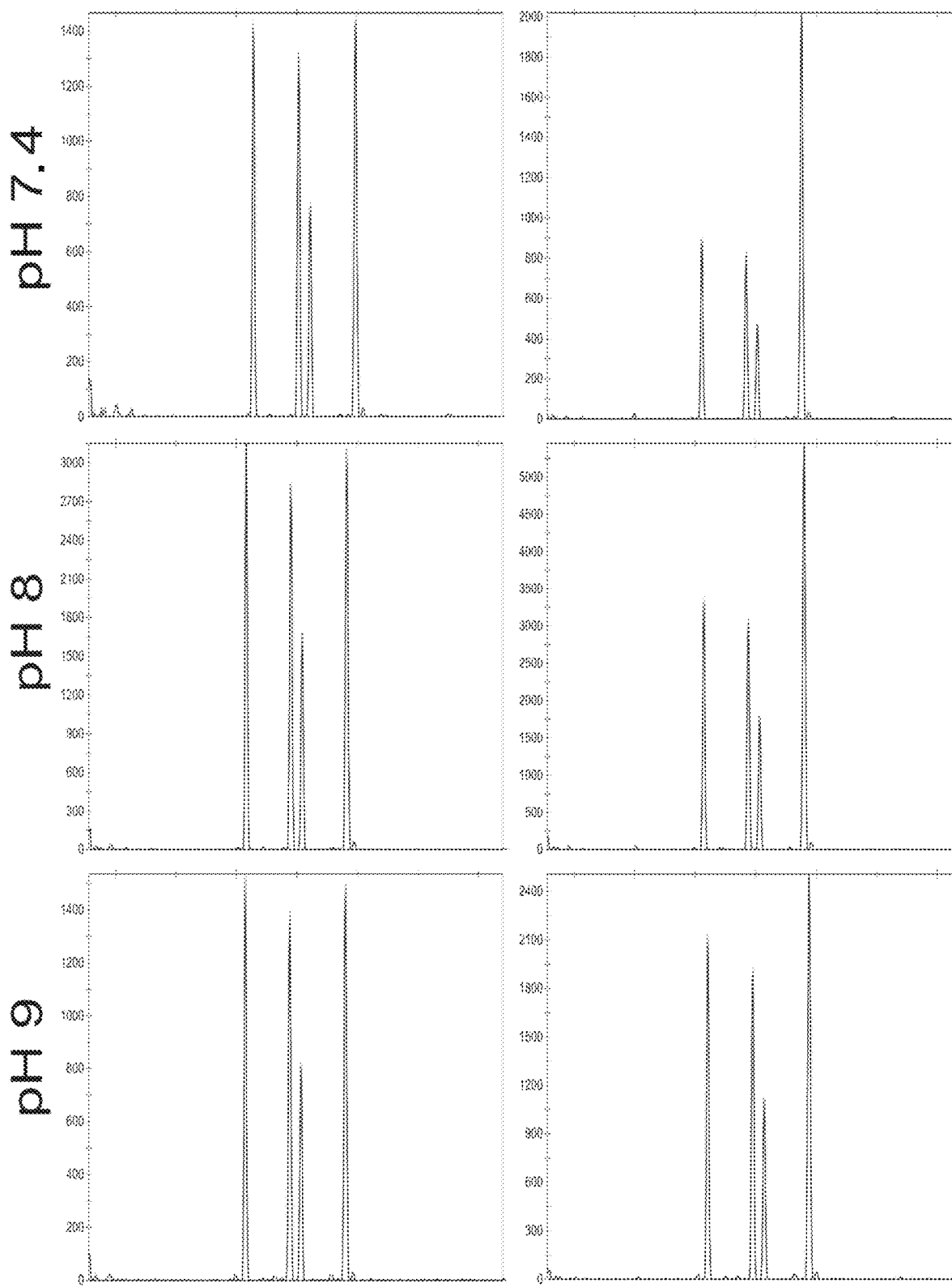

3. Endo S is not IgG Specific in the Presence of Other Immunoglobulin Species that are Desialylated In the present example, it is shown that Endo S is less efficient in cleaving sialylated glycans. It is shown that desialylating the glycans present on the IgA and IgM antibodies results in more non-specific cleavage of sugars by Endo S. Commercial IgG and a mix of IgG, IgA and IgM were incubated with the enzyme *Arthrobacter ureafaciens* alpha-sialidase at pH 5. After desialylation, the buffer was exchanged to obtain the desired pH for carrying out the Endo S digest. Samples that were not desialylated were also compared for Endo S digestion. After Endo S digestion, the samples were dried and labeled with APTS. 2×SEC clean-up was performed and samples were analyzed on the DNA sequencer. As a control, the N-glycans released after Endo S treatment of IgG were desialylated. FIGS. 3A and 3B show that changing the pH of the Endo S buffer does not affect the profile of pure IgG and this is also the case when the IgG is desialylated before Endo S digest. However, changing the pH of the Endo S buffer does affect the profile of IgG, IgA and IgM mix and only until the pH range between 8 and 9 is obtained, does the Endo S enzyme becomes IgG specific. Importantly, when a sialidase digest is performed on the IgG, IgA and IgM mixture prior to Endo S digestion, the pH effect seems to be more pronounced than in the samples that were not desialylated. The latter means that more carbohydrates from IgA and IgM are cleaved by Endo S when the carbohydrates are desialylated and this effect is even seen beyond pH 8 and even beyond pH 9 and no normal IgG profile is obtained when the samples are desialylated. It is believed that the reason why Endo S is considered to be IgG specific in the art is because IgA and IgM are normally present in human serum as highly sialylated proteins.

4. The Efficiency of Endo S Digest Also Depends on the pH

In the present example, it is shown that more carbohydrates are cleaved from IgG with Endo S at pH 8.5 than at pH 7.4. The optimal pH for digest efficiency is pH 8.25. This was investigated in more detail and observed that after 1 hour, up to 95% of all cleavable carbohydrates were cleaved from IgG at pH 8.5.

Figure 4:
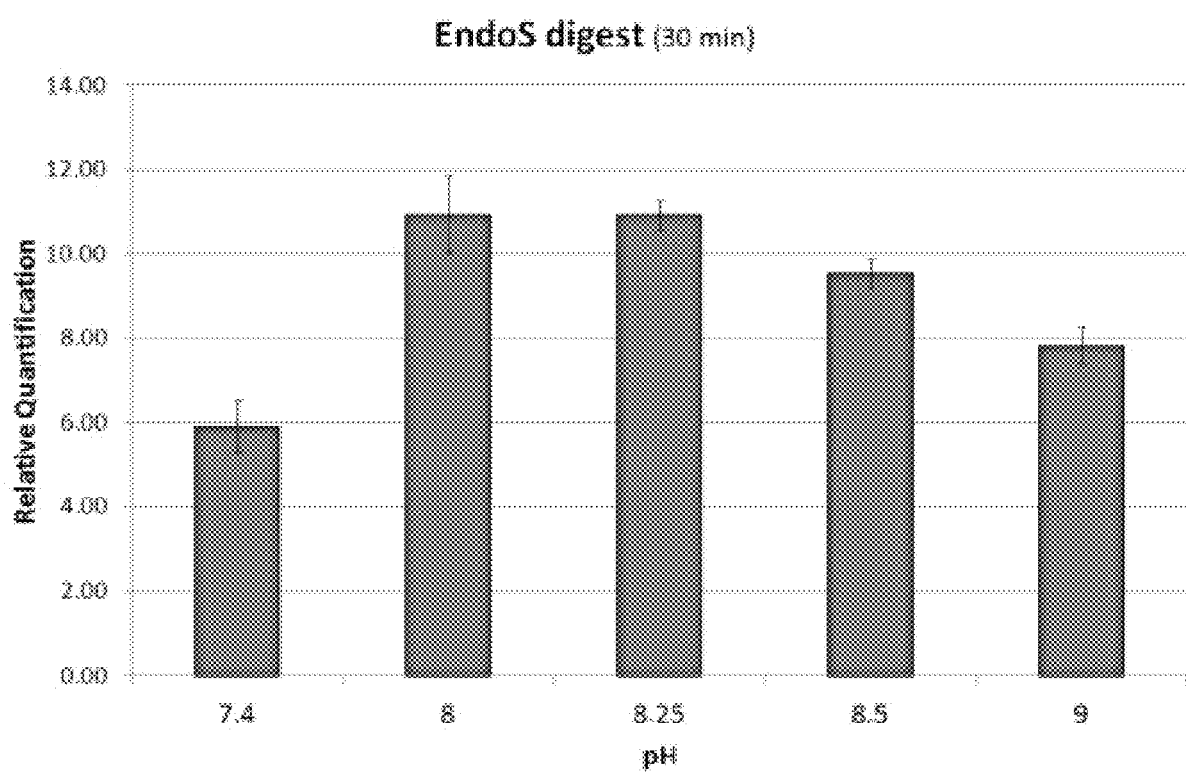
FIG. 4: Relative amount of N-glycans that is cleaved by Endo S in function of the pH of the reaction. The ratio between the Endo S-cleaved glycans and a fixed amount of co-injected standard represents the reaction efficiency. Error bars represent standard deviation of the mean (n=3).

Endo S was incubated for 30 minutes or overnight with pure IgG at different pH ranges. The released carbohydrates were dried and labeled with APTS. The samples were analyzed on the DNA sequencer. Before analysis, an equal amount of maltotetraose standard was added to the samples for relative quantification (the samples were prepared and labeled in triplicate). In FIG. 4, errors represent standard deviation of the mean of the three samples. The highest digest efficiency is observed at pH 8-8.25. Compared to the optimal pH, only 50% to 66% of the carbohydrates are cleaved at pH 7.4 and 9.0, respectively. The amount of released glycans is very similar when incubating 30 minutes compared to an overnight digest (results not shown). pH 8.5 was chosen as the best reaction condition, because the enzyme only cleaves IgG at this pH (see Example 2—Endo S is only IgG specific in serum at pH >8) while still removing up to 90% of the sugars that can be cleaved by Endo S (optimal pH is between 8 and 8.25).

5. Bisecting GlcNAc Modified N-Glycans are not Cleaved by Endo S

In this example, it was found that N-glycans containing a bisecting GlcNAc residue are not cleaved by Endo S at all. Moreover, it was found that an alpha-1,6-fucose is a prerequisite for cleavage. Different concentrations of Endo S were incubated with pure IgG at pH 8.5. The Endo S-treated IgG was then deglycosylated with PNGase F in order to analyze the sugars that were not removed by Endo S. In previous experiments, it was found that NA2FB (see FIG. 5 for the glycan structure) was not cleaved at all and this peak was used to normalize all the peak heights. By comparison with the untreated IgG, the amount of each sugar that was not cleaved by Endo S can be assessed as shown in FIG. 5.

Figure 5:
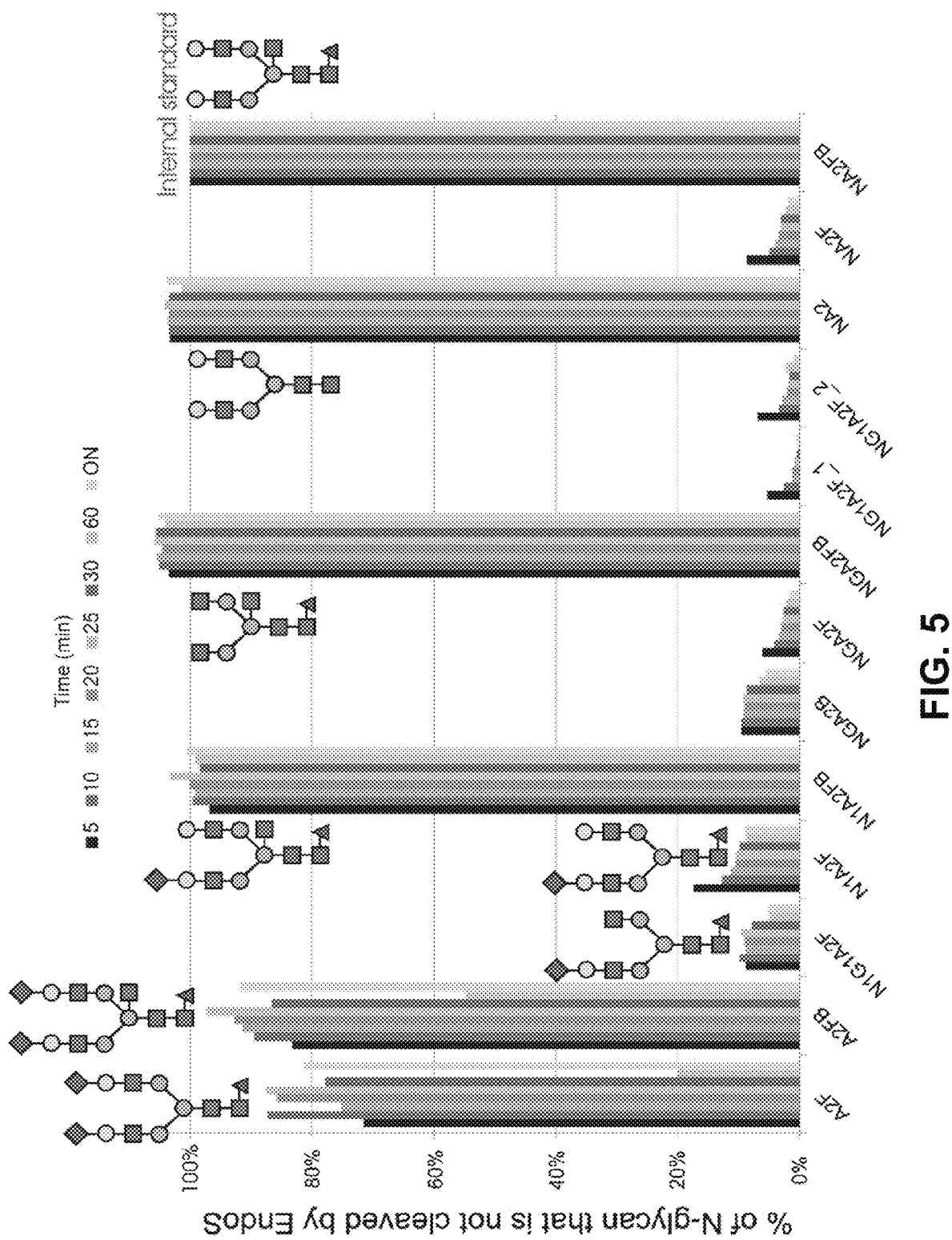
FIG. 5: Relative amount of each N-glycan that remains after Endo S treatment of human IgG. The abundance of each glycan was normalized to the internal standard NA2FB, which is not cleaved by Endo S. The obtained ratio is then compared with that of the untreated IgG and gives the fraction of each N-glycan that has not been cleaved by Endo S (%). 25 µg of human IgG was incubated with 25 units of IgGZero at pH 8.5. According to Genovis, over 95% of the antibody should be deglycosylated within 30 minutes.

FIG. 5 depicts that N-glycans that are fully sialylated are not well cleaved by Endo S (up to 80% still remaining). At a lower pH, Endo S can cleave sialylated structures more efficiently; however, the enzyme is then also much more aspecific. Monosialylated structures are much better substrates (90% cleaved) unless a bisecting GlcNAc residue is present. Neutral sugars are almost completely (98%) removed by Endo S unless a bisecting GlcNAc residue is present (see NGA2Fb and NA2FB in FIG. 5) or no alpha-1,6-fucose is present (see NA2 in FIG. 5). At pH 7.4, recommended by the commercial suppliers, the same substrate specificity is observed.

6. Conclusions of Our Data

The use of Endo S at a pH of 7.4 and lower on human serum results in
- Non-specific cleavage of sialylated sugars from other serum proteins.
- Non-specific cleavage of unsialylated sugars from other serum proteins (in particular, IgA and IgM) in patients with lower sialylation levels.
- Incomplete digest of IgG N-glycans.

It is concluded that the use of Endo S at a pH of 7.4 and lower leads to an incorrect measurement of IgG undergalactosylation and, hence, that a pH higher than 7.4 needs to be used.

7. Diagnostic Utility of Endo S for Measuring Underglactosylation of Proteins In the previous examples, mainly the specificity of Endo S for IgG in serum was investigated. In this example, the investigation was to determine whether measuring undergalactosylation (UGS) using Endo S correlates well with the actual IgG galactosylation (the golden standard to determine UGS is obtained after PNGase F digestion). A second question was to determine whether using Endo S at pH 8.5 correlates better with the IgG UGS compared to the use of Endo S at the recommended pH, i.e., pH 7.4.

Therefore, the sera of healthy volunteers (n=8) with low IgG undergalactosylation and patients (n=8) with a presumed high level of IgG undergalactosylation was analyzed. Endo S digest was performed on serum from the patients and on their purified IgG at pH 7.4 or pH 8.5. Also, PNGase F digest was performed on the purified IgG fraction. Endo S profiles from capillary electrophoreses were obtained after labeling and cleanup of the sugars and compared with PNGase F treatment of purified IgG from the same samples.

Undergalactosylation (UGS 1) was calculated according to the art for the use of PNGase F using the specific amount of glycans as follows:

$$UGS\ 1 = \frac{\left(\begin{array}{c}2*(NGA2 + NGA2F + NGA2FB) + \\ (NG1A2F\_1 + NG1A2F\_2)\end{array}\right)}{\left(\begin{array}{c}2*\ \ (NGA2 + NGA2F + NGA2FB + NG1A2F\_1 + NG1A2F\_2 + \\ NA2 + NA2F + NA2FB) + 3*(NA3++NA3Fb)\end{array}\right)}$$

Undergalactosylation determined with Endo S (UGS 4) was calculated using the specific amount of glycans as follows:

$$UGS\ 4 = \frac{(2*(NGA2F^*)) + (NG1A2F\_1^* + NG1A2F\_2^*)}{(2*(NGA2F^* + NG1A2F1^* + NG1A2F2^* + NA2F^*))}$$

In order to be able to compare the undergalactosylation of PNGase F profiles with Endo S profiles, only the peaks from sugars that can be cleaved by Endo S (i.e., NGA2F|NG1A2F_1_|NG1A2F_2|NA2F) were used for the calculation. The sugar codes are the same as used in the previous experiments. Correlation of UGS 4 with the traditional way of measuring UGS (UGS 1, where all peaks are used in the calculation) was also tested in this experiment.

A simplified and preferred version of these scores is to calculate the ratio of the completely non-galactosylated NGA2F* and galactosylated NA2F* in the N-glycan profile resulting after an Endo S digest (see further in Example 10).

Figure 6:
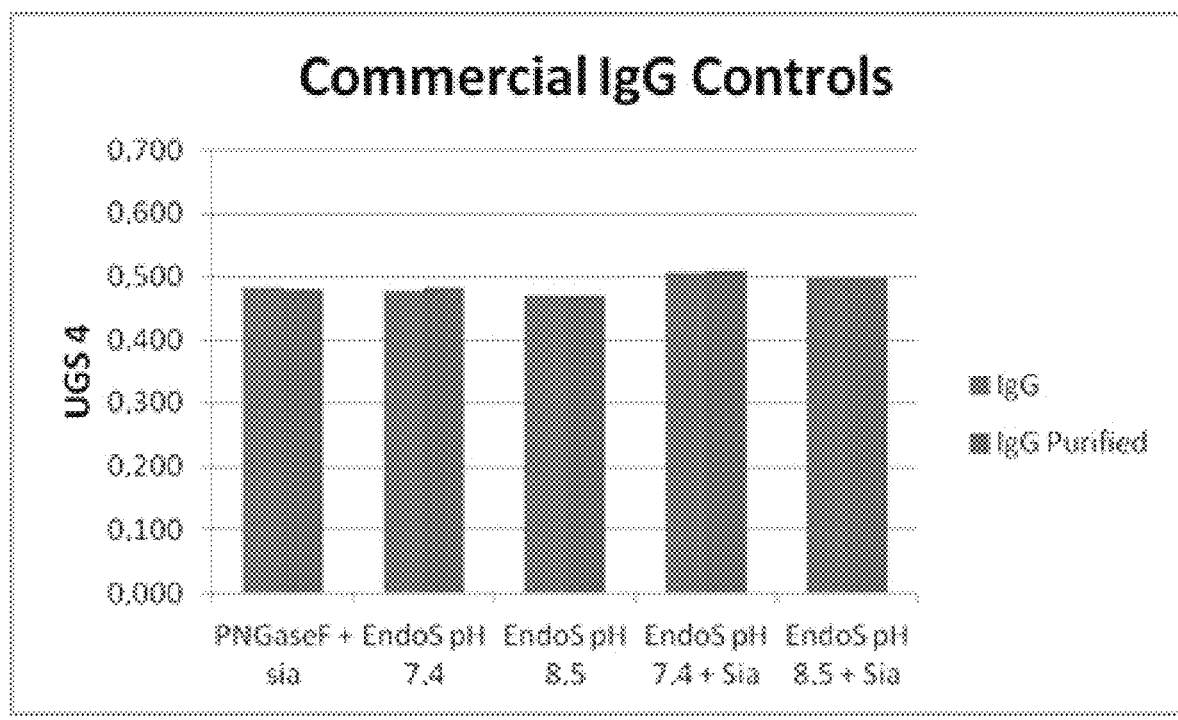
FIG. 6: Undergalactosylation of commercial IgG before and after IgG purification. UGS4 is shown for different substrate conditions.

In FIG. 6, the controls show that the purification procedure did not affect undergalactosylation and that the UGS 4 score is the same for the PNGase F profiles as for the Endo S profiles. This means that the UGS 4 score can be used to compare undergalactosylation between PNGase F profiles of purified IgG and Endo S profiles obtained from serum.

7.1 Correlations with the Golden Standard

Figure 7A:
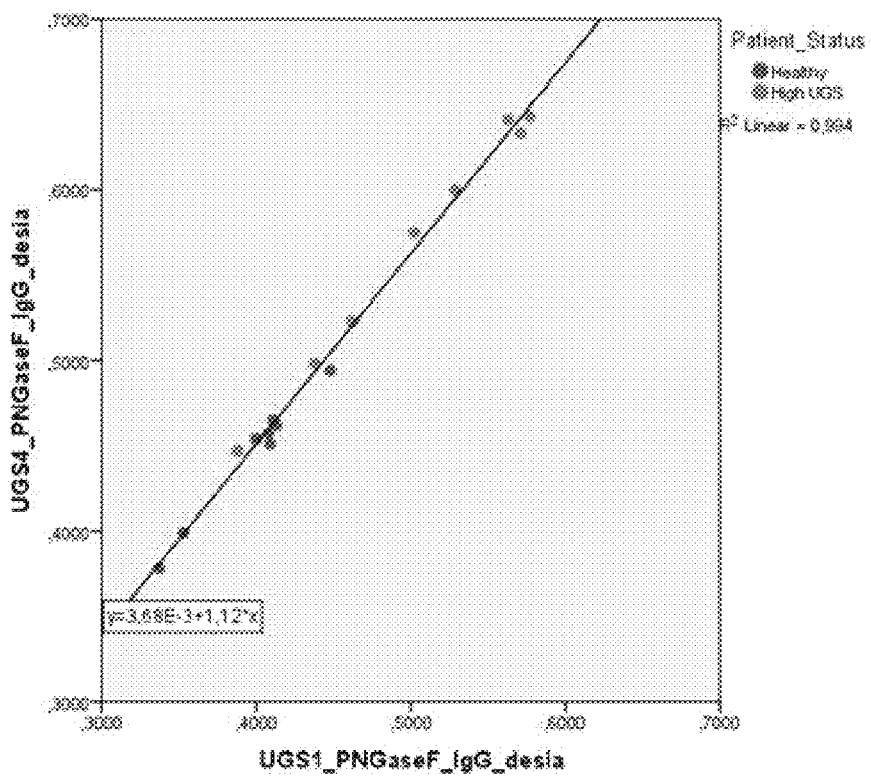
FIGS. 7A-7D: Linear regression scatter plots.

Undergalactosylation calculated in the traditional way (UGS 1) of PNGase F profiles of IgG (desialylated) correlates very well with UGS 4 calculated on the same profiles with Spearman Rho=0.982 (see FIG. 7A).

Figure 7B:
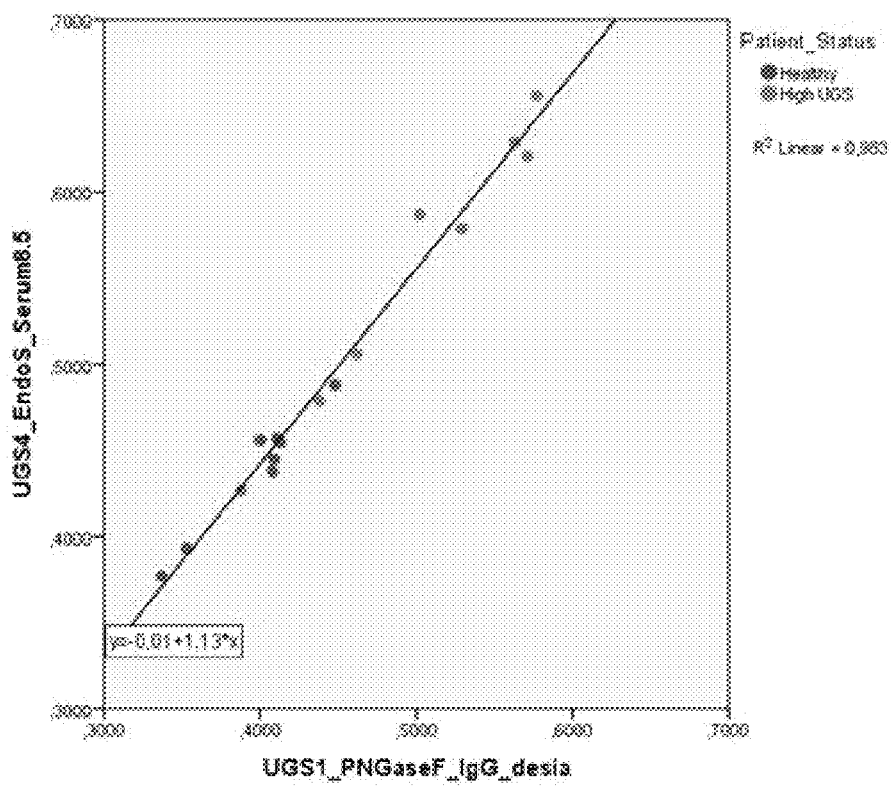

UGS 1 of PNGase F-treated IgG (desialylated) also correlates very well with UGS 4 of Endo S profiles of serum (pH 8.5/sialylated) with Spearman Rho=0.971 (see FIG. 7B).

Figure 7C:
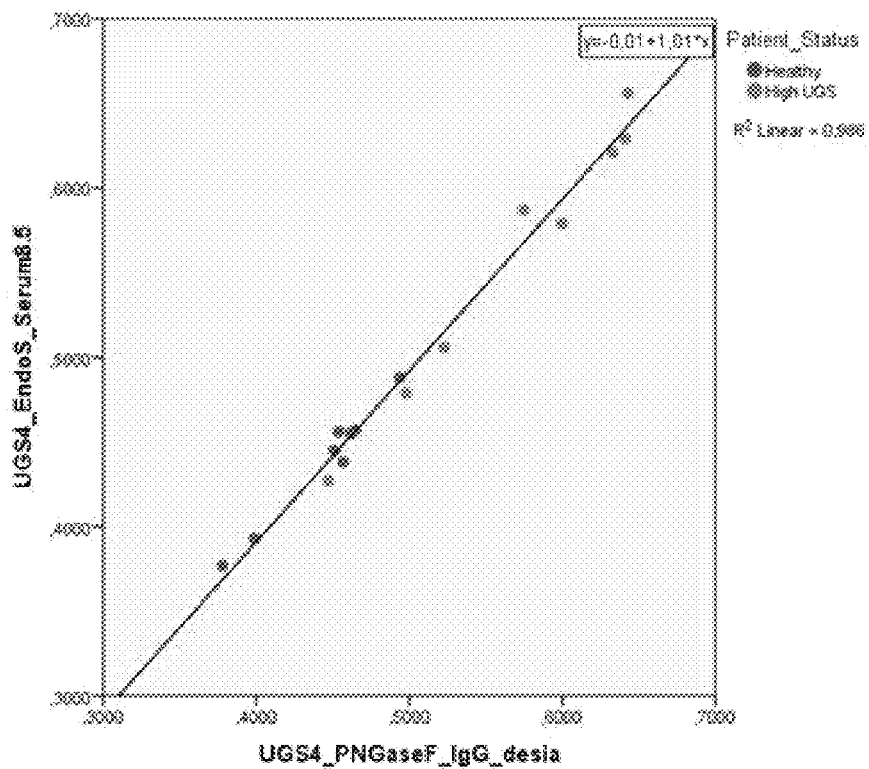

UGS 4 of PNGase F profiles of IgG also correlates very well with UGS 4 of Endo S profiles of serum (pH 8.5/sialylated) with Spearman Rho=(0.979 see FIG. 7C). Furthermore, not only do the values correlate, their absolute values also approximately match.

Figure 7D:
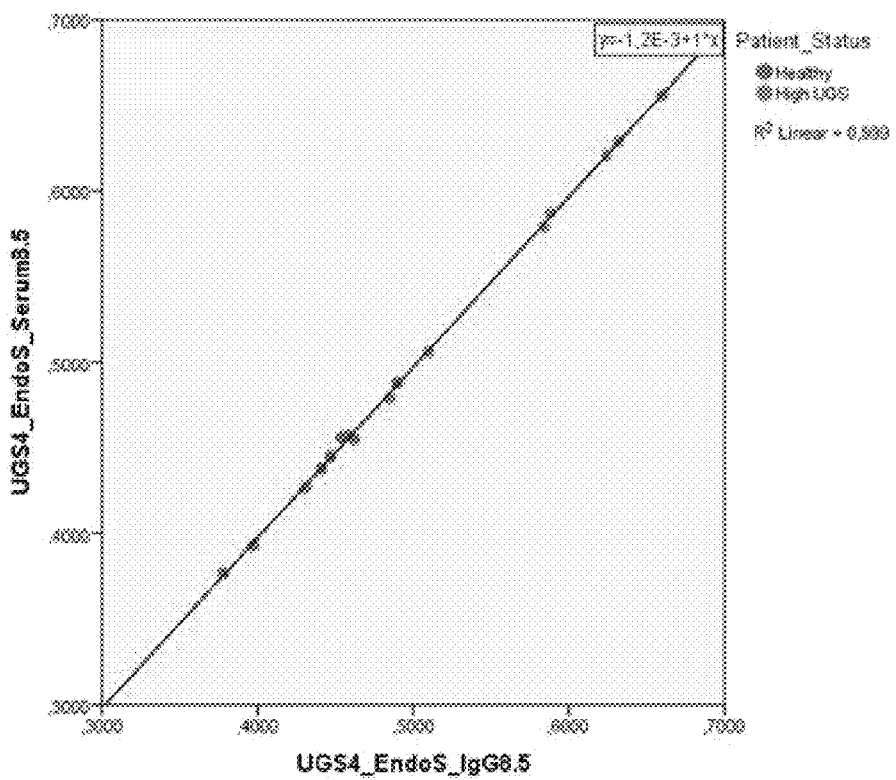

UGS 4 of Endo S profiles of IgG also correlates very well with UGS 4 on Endo S profiles of serum with Spearman Rho=0.991 (see FIG. 7D). This means that, using Endo S, one specifically measures IgG undergalactosylation in serum.

7.2 Conclusions

The undergalactosylation level obtained with Endo S on serum (UGS4) correlates very well with the golden standard PNGase F on purified IgG (UGS1). This is rather unexpected since not all glycan species are cleaved by Endo S. Indeed, the examples show that certain glycan species are not cleaved by Endo S (in contrast to PNGase F), even under pH optimized conditions. Endo S digestion is therefore not reflecting the exact full IgG glycan profile. However, unexpectedly the UGS of Endo S (UGS4) correlates very well with the UGS obtained after digestion with PNGase F (UGS1). We conclude that the use of Endo S is a reliable alternative method to measure IgG undergalactosylation.

The method of calculating undergalactosylation (UGS4) based on Endo S profiles not only correlates with the UGS4 calculated on PNGaseF-obtained profiles, but the absolute values also approximately match. The latter is not trivial since investigation as to which sugars are cleaved by Endo S needed to be performed before obtaining the formula for calculating UGS4.

It is clear that the use of Endo S at pH 8.5 results in more specific and efficient cleaving of IgG sugars. This aspect is particularly relevant in patients who have a high level of IgA or IgM in their serum because IgA and IgM is shown here to be non-specifically cleaved by Endo S at lower pH and this has an effect on the measured UGS.

8. Diagnostic Utility of Endo S for Measuring Undergalactosylation of Proteins (Large Cohort)

Figure 9:
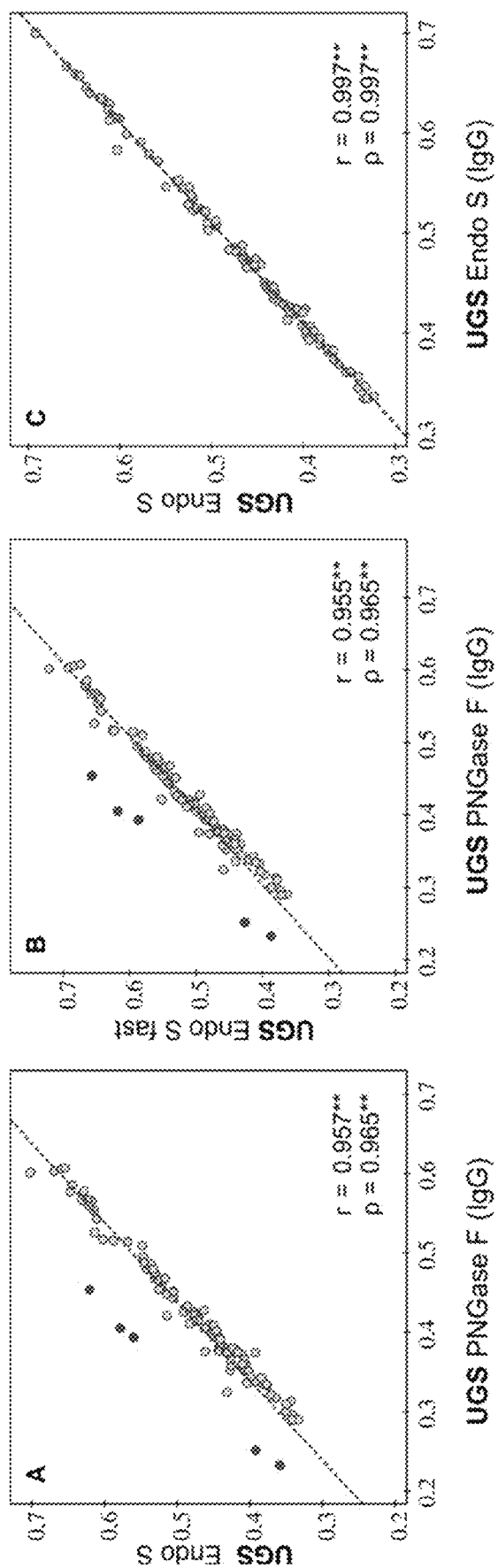
FIG. 9: Reliability of UGS measurement with Endo S in serum. Serum and serum-purified IgG from 96 individuals were analyzed by using Endo S and PNGase F. Undergalactosylation was calculated and scatterplots am shown for the different combinations. Pearson's r and Spearman's rho correlation coefficients are shown in the scatterplots. The left panel shows the UGS obtained after Endo S digestion on the mixture of total proteins present in serum versus the UGS obtained after PNGase F on purified IgG. The middle panel shows the same correlation except for the fact that after the Endo S digest, no separation between the obtained glycans and proteins is carried out (fast protocol as explained in Example 8). The right panel shows the correlation of UGS obtained after Endo S digest on the total mixture of proteins present in serum versus the Endo S digest carried out on purified IgG.

In the present example, serum (the total mixture of proteins present in the serum) and serum-purified IgG from 96 patients was digested by Endo S (see materials and methods for the complete protocol). In parallel, there was also a PNGase F digest performed on serum-purified IgG from the corresponding samples. A fraction of the sample volume was labeled according to the standard protocol and desialylated prior to DNA sequencer analysis (see materials and methods). The other fraction was labeled using a fast protocol, which only takes one hour, and no sialidase digest or clean-up (i.e., after the Endo S digest, the obtained glycans were not separated from the remaining proteins in the serum sample) was performed before CE analysis (see middle panel in FIG. 11). Pearson's r and Spearman's p correlation coefficients were calculated from the obtained UGS scores and the data was visualized in scatterplots. A very high correlation between UGS determined by Endo S and UGS determined by PNGase F was found (see FIG. 9, left panel).

Five outliers of linear regression were detected by studentized residual plot >2. These outliers showed NA3 in the corresponding PNGase F CE profile, which points to suboptimal IgG purification of these serum samples. These outliers were not found when Endo S was performed on the purified IgG samples (see right panel of FIG. 9).

9. Diagnostic Performance of the Method of the Disclosure for the Diagnosis of NASH In this disclosure, 39 patients were analyzed for which a biopsy, K18F analysis and GlycoNASHTest data were available. K18F is reported as the best available serological marker for NASH (see, e.g., Y. Yilmaz et al. (2009), *World J. Gastroenterol.* 15(35) 4387-4391), whereas GlycoNASH-Test (GNT) has recently been suggested by Blomme et al. (2012), *Dig. Liver Dis.* 44:315-322) (1). The latter is the log-transformed ratio between NGA2F and NA2 in the desialylated N-glycan profile of serum. An Endo S digest was performed, as well as a PNGase F digest on the serum samples. The UGS and GlycoNASHTest were calculated from the resulting CE glycan profiles. The diagnostic efficiency of the three markers to distinguish between NASH (n=14) and patients with either steatosis (n=15) or borderline NASH (n=10) was tested using a ROC analysis.

Figure 10:
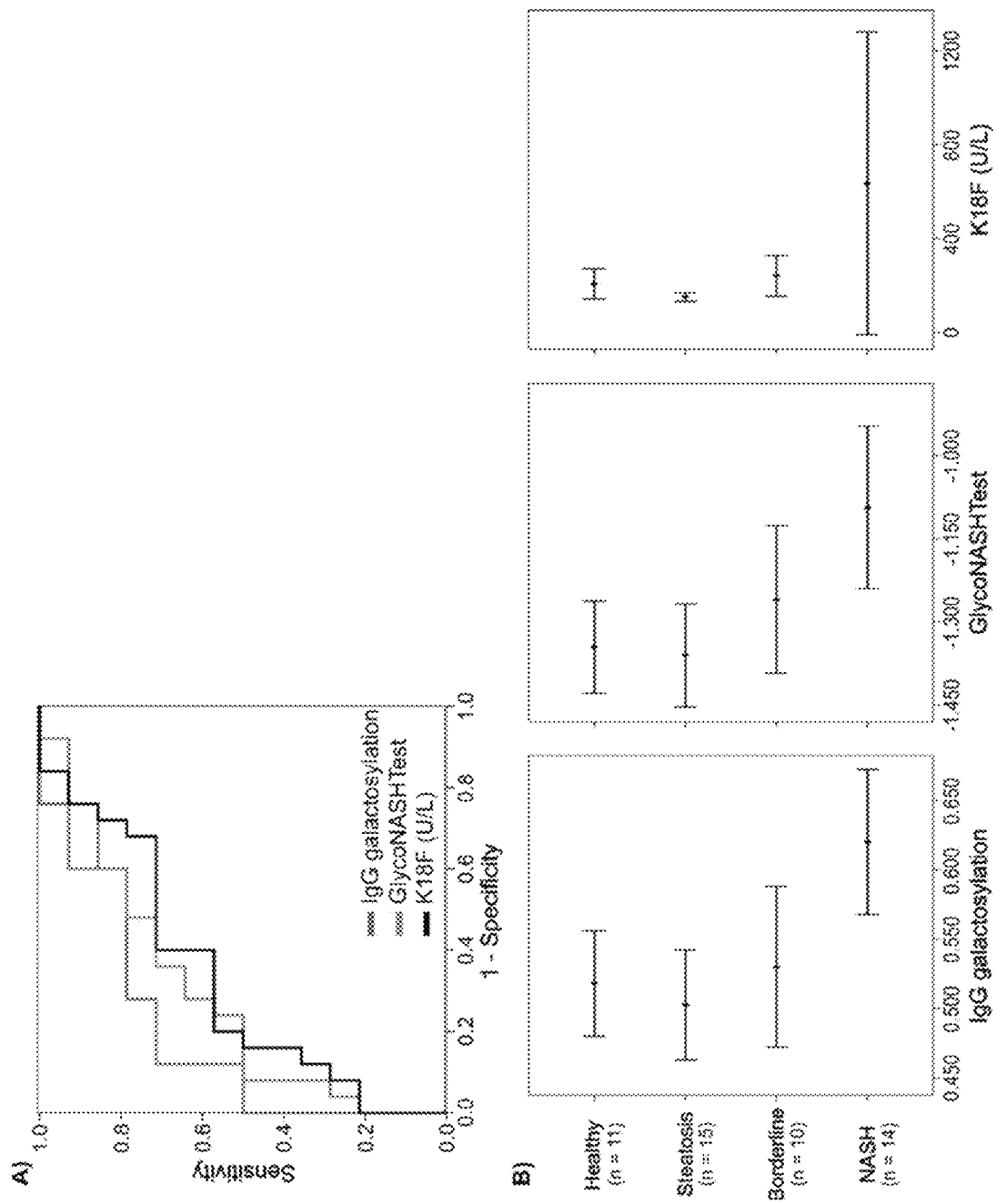
FIG. 10: Diagnostic performance of UGS in NASH detection compared to GlycoNASHTest and K18F. ROC curve and 95% confidence intervals are shown.

The results clearly show that the IgG galactosylation measured with Endo S performs better for diagnosing NASH than GlycoNASHTest and K18F (see FIG. 10). In addition, the AUC for the Endo S marker (0.78; [0.62-0.95], 95% CI) is higher than that of the GlycoNASHTest (0.75; [0.58-0.92], 95% CI) and especially better than for the K18F test (0.68; [0.49-0.86], 95% CI). K18F measurements show a more pronounced scatter in the NASH group compared to the IgG galactosylation marker and GlycoNASHTest. Based on these plots, the overlap between borderline and NASH patients is also smaller for the Endo S marker compared to GlycoNASHTest.

10. Diagnosis of NASH Based on the Monitoring of Under-Galactosylation

In the present example, 49 patients who underwent bariatric surgery for obesity, with varying degrees of non-alcoholic fatty liver disease, liver histology were examined for lobular inflammation according to D. E. Kleiner et al. (2005), *Hepatol. Baltim. Md* 41, 1313-1321) and staged as follows: 0="no inflammatory foci," 1="<2 foci," 2="2-4 foci," 3=">4 foci." Serum samples from these individuals were processed with the EndoS-based methodology of the disclosure (see materials and methods) and the resulting N-glycan profiles were quantified. A simple undergalactosylation score based on the log-transformed ratio between the peak height of the fully agalactosylated glycan NGA2F* and the fully galactosylated glycan NA2F* was calculated and plotted vs. the histologically determined lobular inflammation stage. Error bars indicate the 95% confidence interval for the mean in FIG. 11. A clear progressive increase in this undergalactosylation score with increasing levels of lobular inflammation is seen.

Materials and Methods

1. Patients

Serum samples from 96 NAFLD patients, enlisted for bariatric surgery, were obtained from an outpatient clinic (Ghent University Hospital) and stored at −20° C. Informed consent was given by all patients and the protocol was approved by Ghent University Hospital's Ethics Committee. All patients had a BMI of at least 30 kg/m$^2$, were negative for viral hepatitis and auto-immune conditions and showed an alcohol intake of less than 100 or 200 g per week for men and women, respectively. A subset of the patients underwent a wedge liver biopsy for histological analysis by a pathologist. Thirteen patients showing no steatosis, ballooning or fibrosis were diagnosed as healthy. The NAFLD activity score (NAS) was used to classify the NAFLD patients in a steatosis (NAS <3; n=22), borderline NASH (NAS 3-4; n=10) and NASH group (NAS of >5; n=18). Histological features were scored according to D. E. Kleiner et al. (2005), *Hepatology* 41, 1313-1321). An ELISA was performed to determine the serum concentration of K18F in units per liter (PEVIVA AB, Bromma, Sweden). A fraction of these patients (51 out of 96) have been described in a previous study (B. Blomme et al. (2012), *Dig. Liver Dis.* 44:315-322). For some analysis, only those patients were retained for which a K18F test result was available, and for correlation with liver histology, only those patients were retained for whom such histological evaluation was available.

2. IgG Glycan Release, Labeling and Analysis

Lyophilized recombinant Endo S with the product name IgGZERO™ was purchased from Genovis and reconstituted in ultrapure water at 20 U/µl. 2.5 µl of patients' serum and 25 U of Endo S were combined in a total volume of 10 µl with final buffer concentrations of 150 mM NaCl and 50 mM Tris-HCl pH 8.5. The mixture was incubated in a PCR thermocycler for 1 hour at 37° C.

Digested serum, without any purification and, thus, still containing serum components, enzyme and buffer components was then directly labeled fluorescently with 8-aminopyrene-1,3,6-trisulphonic acid (APTS) and analyzed by capillary electrophoresis. 5 µl of labeling solution (a 1:1 v/v mix of 350 mM APTS in 2.4 M citric acid/14% SDS and 1 M of a borohydride reductant in 20% DMSO/4 M Urea/20% SDS/40 mM NH$_4$Ac pH 5) was added to 5 µl of crude digest. Samples were then incubated in a PCR thermocycler for 1 hour at 70° C. Labeled samples were quenched in 90 µl ultrapure water and, if necessary, further diluted to keep the signal within the dynamic range of the detector. The (diluted) samples were analyzed on an ABI3130 DNA sequencer using the standard protocol for N-glycan analysis as described earlier (W. Laroy et al. (2006), *Nat. Protoc.* 1:397-405).

REFERENCES

1. Parekh R. B., R. A. Dwek et al. (1985). Association of rheumatoid arthritis and primary osteoarthritis with changes in the glycosylation pattern of total serum IgG. *Nature* 316:452-457.
2. Saldova R., M. R. Wormald, R. A. Dwek, and P. M. Rudd (2008). Glycosylation changes on serum glycoproteins in ovarian cancer may contribute to disease pathogenesis. *Dis. Markers* 25:219-232.
3. Pilkington C., E. Yeung, D. Isenberg, A. K. Lefyert, and G. A. Rook (1995). Agalactosyl IgG and antibody specificity in rheumatoid arthritis, tuberculosis, systemic lupus erythematosus and myasthenia gravis. *Autoimmunity* 22(2):107-111.
4. Go M. F., R. E. Schrohenloher, and M. Tomana (1994). Deficient galactosylation of serum IgG in inflammatory bowel disease: correlation with disease activity. *J. Clin. Gastroenterol.* 18(1):86-87.
5. Vanderschaeghe D., W. Laroy, E. Sablon, P. Halfon, A. Van Hecke, J. Delanghe, and N. Callewaert (2009). GlycoFibrotest is a highly performant liver fibrosis biomarker derived from DNA sequencer-based serum protein glycomics. *Mol. Cell. Proteomics* 8(5):986-994.
6. Van Beneden K., K. Coppieters, W. Laroy et al. (2009). Reversible changes in serum immunoglobulin galactosylation during the immune response and treatment of inflammatory autoimmune arthritis. *Ann. Rheum. Dis.* 68(8):1360-1365.
7. Ho C. H., R. N. Chien, P. N. Cheng, J. H. Liu, et al. (2015). Aberrant serum immunoglobulin G glycosylation in chronic hepatitis B is associated with histological liver damage and reversible by antiviral therapy. *J. Infect. Dis.* 211(1):115-124.
8. Collin M. and A. Olsén (2001). EndoS, a novel secreted protein from *Streptococcus pyogenes* with endoglycosidase activity on human IgG. *EMBO J.* 20:3046-55.
9. Trastoy B., J. V. Lomino, B. G. Pierce, L. G. Carter, S. Günther, J. P. Giddens, G. A. Snyder, T. M. Weiss, Z. Weng, L.-X. Wang and E. J. Sundberg (2014). Crystal structure of *Streptococcus pyogenes* EndoS, an immunomodulatory endoglycosidase specific for human IgG antibodies. *Proc. Natl. Acad. Sci. U.S.A* 111:6714-9.
10. Allhorn M., A. I. Olin, F. Nimmerjahn and M. Colin (2008). Human IgC/FcγR interactions are modulated by streptococcal IgG glycan hydrolysis. *PLoS One* 3(1): e1413.
11. Nandakumar S., M. Collin, K. E. Happonen, A. M. Croxford, S. L. Lundström, R. A. Zubarev, M. J. Rowley and A. M. Blom (2014). Retraction for Nandakumar et al., Dominant suppression of inflammation by glycan-hydrolyzed IgG. *Proc. Natl. Acad. Sci. U.S.A.* 111:15851.
12. Collin M., O. Shannon and L. Björck (2008). IgG glycan hydrolysis by a bacterial enzyme as a therapy against autoimmune conditions. *Proc. Natl. Acad. Sci. U.S.A.* 105:4265-4270.

The invention claimed is:

1. A method of diagnosing or prognosing inflammation in a mammal, the method comprising:
    digesting N-linked glycans present on a total mixture of glycoproteins present in a body fluid with Endoglycosidase S at a pH between 8.5 and 9.0 to obtain a profile of N-linked glycans, wherein the body fluid is derived from the mammal and consists of blood, serum, and/or plasma,
    determining the ratio between at least one non-galactosylated N-glycan and at least one galactosylated N-glycan present in the profile of N-linked glycans; and
    attributing at least a 5% difference in the ratio, as compared to the same ratio determined for a mammal not suffering from inflammation or the same ratio obtained from a mammal suffering from inflammation before receiving therapy, with the presence or prognosis of inflammation.

2. The method according to claim 1, wherein determining the ratio between at least one non-galactosylated N-glycan and at least one galactosylated N-glycan present in the profile of N-linked glycans is carried out without purifying N-glycans from the totamixture.

3. The method according to claim 1, wherein the ratio between the at least one non-galactosylated N-glycan and the at least one galactosylated glycan is the ratio between:
    GlcNAc(β-1,2)Man(α-1,3)[GlcNAc(β-1,2)Man(α-1,6)]Man(β-1,4)GlcNAc (NGA2F*) and
    Gal(β-1,4)GlcNAc(β-1,2)Man(α-1,3)[Gal(β-1,4)GlcNAc(β-1,2)Man(α-1,6)]Man(β-1,4)GlcNAc (NA2F*).

4. The method according to claim 2, wherein the ratio between the at least one non-galactosylated N-glycan and the at least one galactosylated glycan is the ratio between:
    GlcNAc(β-1,2)Man(α-1,3)[GlcNAc(β-1,2)Man(α-1,6)]Man(β-1,4)GlcNAc (NGA2F*) and
    Gal(β-1,4)GlcNAc(β-1,2)Man(α-1,3)[Gal(β-1,4)GlcNAc(β-1,2)Man(α-1,6)]Man(β-1,4)GlcNAc (NA2F*).

5. The method according to claim 1, wherein the mammal has non-alcoholic fatty liver disease (NAFLD), non-alcoholic steatohepatitis (NASH), rheumatoid arthritis, osteoarthritis, psoriatic arthritis, ankylosing spondylitis, Crohn's Disease, colitis, ulcerative colitis, or any combination of any thereof.

6. The method according to claim 2, wherein the mammal has non-alcoholic fatty liver disease (NAFLD), non-alcoholic steatohepatitis (NASH), rheumatoid arthritis, osteoarthritis, psoriatic arthritis, ankylosing spondylitis, Crohn's Disease, colitis, ulcerative colitis, or any combination of any thereof.

7. The method according to claim 3, wherein the mammal has non-alcoholic fatty liver disease (NAFLD), non-alcoholic steatohepatitis (NASH), rheumatoid arthritis, osteoarthritis, psoriatic arthritis, ankylosing spondylitis, Crohn's Disease, colitis, ulcerative colitis, or any combination of any thereof.

8. The method according to claim 4, wherein the mammal has non-alcoholic fatty liver disease (NAFLD), non-alcoholic steatohepatitis (NASH), rheumatoid arthritis, osteoarthritis, psoriatic arthritis, ankylosing spondylitis, Crohn's Disease, colitis, ulcerative colitis, or any combination of any thereof.

* * * * *